US012790309B2

(12) United States Patent
Elsohly et al.

(10) Patent No.: US 12,790,309 B2
(45) Date of Patent: Nov. 10, 2026

(54) CANNABICHROMENE DERIVATIVES AND METHODS FOR MAKING AND USING THE SAME

(71) Applicant: University of Mississippi, University, MS (US)

(72) Inventors: Mahmoud A. Elsohly, Oxford, MS (US); Waseem Gul, Oxford, MS (US); Nicole Marie Ashpole, Tupelo, MS (US); Hannah Harris, New York, NY (US)

(73) Assignee: University of Mississippi, University, MS (US)

(*) Notice: Subject to any disclaimer, the term of this patent is extended or adjusted under 35 U.S.C. 154(b) by 376 days.

(21) Appl. No.: 18/574,939

(22) PCT Filed: Jun. 30, 2022

(86) PCT No.: PCT/US2022/035752
§ 371 (c)(1),
(2) Date: Dec. 28, 2023

(87) PCT Pub. No.: WO2023/278719
PCT Pub. Date: Jan. 5, 2023

(65) Prior Publication Data

US 2024/0336587 A1 Oct. 10, 2024

Related U.S. Application Data

(60) Provisional application No. 63/217,401, filed on Jul. 1, 2021.

(51) Int. Cl.

| | |
|---|---|
| ***C07D 311/58*** | (2006.01) |
| ***A61K 31/352*** | (2006.01) |
| ***A61P 29/00*** | (2006.01) |

(52) U.S. Cl.
CPC .......... *C07D 311/58* (2013.01); *A61K 31/352* (2013.01); *A61P 29/00* (2018.01)

(58) Field of Classification Search
None
See application file for complete search history.

(56) References Cited

U.S. PATENT DOCUMENTS

2019/0142888 A1 5/2019 Mojsa

FOREIGN PATENT DOCUMENTS

| | | | |
|---|---|---|---|
| WO | 2020051284 A1 | 3/2020 | |
| WO | WO-2022213200 A1 * | 10/2022 | ............. A61K 31/27 |

OTHER PUBLICATIONS

De La Torre et al: "Synthesis of ( )- O-methylcannabichromene and some homologues", Journal of Heterocyclic Chemistry, vol. 18, No. 6, Oct. 1, 1981 (Oct. 1, 1981), pp. 1251-1252, XP093261128, US ISSN: 0022-152X, DOI: 10.1002/jhet.5570180637.

Yagen B et al: "Stereospecific cyclizations and isomerizations of cannabichromene and related cannabinoids.", Tetrahedron Letters, vol. 10, No. 60, Dec. 1, 1969 (Dec. 1, 1969), pp. 5353-5356, XP093261187.

Extended European Search Report for EP 22834233.3 mailed Apr. 4, 2025.

International Search Report for PCT/US2022/035752 mailed Sep. 18, 2022.

Radwan, et al., "Cannabinoids Phenolics, Terpenses and Alkafolds of Cannabis, Molecules", vol. 26, No. 2774. May 8, 2021.

* cited by examiner

*Primary Examiner* — Valerie Rodriguez-Garcia
*Assistant Examiner* — Jed A Kucharczk
(74) *Attorney, Agent, or Firm* — Thomas | Horstemeyer, LLP

(57) ABSTRACT

Described herein are new derivatives of cannabichromene that are effective in treating or preventing pain in a subject. The new cannabichromene derivatives have improved bioavailability, which enhances their ability to treat or prevent pain. In one aspect, the cannabichromene derivatives have the structure I or the pharmaceutically acceptable salt thereof. Also described herein are methods for making and using the cannabichromene derivatives.

20 Claims, 30 Drawing Sheets

Valine
Valine Allyl
Valine Allyl
Cannabichromene (CBC)
CBC-valine-allyl
CBC-valine-allyl
CBC-valinate
CBC-valinate
CBC-valine-hemisuccinate HPLC chromatogram of CBC-VHS showing two peaks for CBC-VHS isomers on Phenomenex Luna C18(2) column (150x4.6) 3 micron (77 % ACN:23% water, both having 0.1% Formic acid at 30°C, 0.8 mL/minute flow rate)

HPLC chromatogram of CBC-VHS showing two peaks for CBC-VHS isomers on Phenomenex Luna C18(2) column (150x4.6) 3 micron (67 % ACN:33% water, both having 0.1% Formic acid at 30°C, 0.8 mL/minute flow rate)

HPLC chromatogram of CBC-VHS showing two peaks for CBC-VHS isomers on Phenomenex Luna C18(2) column (250x4.6) 5 micron (65 % ACN:35% water, both having 0.1% Formic acid at 30°C, 0.8 mL/minute flow rate)

HPLC chromatograms of CBC-VHS (A: Full chromatogram and B: expanded chromatogram) showing two peaks for CBC-VHS isomers on Phenomenex Luna C18(2) column (250x10) 5 micron (65 % ACN:35% water, both having 0.1% Formic acid at 30°C, 5.67 mL/minute flow rate)

CANNABICHROMENE DERIVATIVES AND METHODS FOR MAKING AND USING THE SAME

CROSS-REFERENCE TO RELATED APPLICATIONS

This application is the 35 U.S.C. § 371 national stage application of PCT Application No. PCT/US2022/035752, filed Jun. 30, 2022, which application claims the benefit of U.S. Provisional Application No. 63/217,401, filed on Jul. 1, 2021, both of which are hereby incorporated by reference herein in their entireties.

BACKGROUND

Pain is a multifaceted condition with a variety of etiologies[1] and pharmacological treatments. Pain prevalence among US adults has increased 25% since 2007, with 68 million adults reporting pain interfering with daily activities.[2] While opioids are the "Gold Standard" in pain management,[1] they are not without their shortcomings. Approximately 80% of patients treated with opioids suffer from adverse side effects[3] such as sedation, respiratory depression, nausea, constipation, dependence, and the potential of addiction. In 2018, opioids were involved in nearly 70% of the 67,367 drug-related deaths in the United States.[4] The on-going crisis surrounding the over-prescription and abuse of narcotics has quickly driven research towards alternative pain management strategies, particularly in the direction of cannabinoids and their therapeutic potential.[5]

Cannabichromene (CBC), a minor non-psychotropic constituent of marijuana, has previously been reported to have mild anti-inflammatory, or anti-edematous properties when tested in vivo through the carrageenan-induced[14,15] and LPS-induced paw edema models.[16] However, these studies were restricted to high doses of over 100 mg/kg. At far lower doses, CBC displayed protective activity in vivo against an experimental model of intestinal inflammation.[17]

Additionally, CBC has exhibited biphasic anti-nociceptive effects in the tail-flick assay, although this effect was time-dependent.[18] Conversely, some studies have failed to observe anti-nociceptive activity[16] or anti-inflammatory activity[19] with CBC.

SUMMARY

Described herein are new derivatives of cannabichromene that are effective in treating or preventing pain in a subject. The new cannabichromene derivatives have improved bioavailability, which enhances their ability to treat or prevent pain. In one aspect, the cannabichromene derivatives have the structure I or the pharmaceutically acceptable salt thereof

I

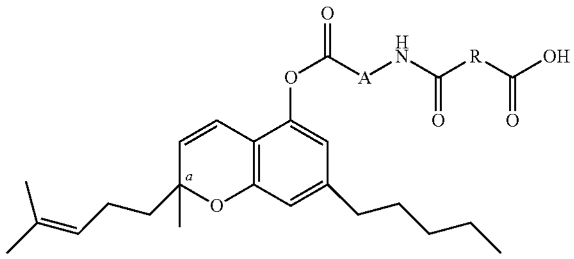

wherein

A is a residue of an amino acid or an alkyl group;

R is an alkyl group or an aryl group; and the stereochemistry at carbon a is substantially R, substantially S, or racemic.

Also described herein are methods for making and using the cannabichromene derivatives.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION

Figure 1:
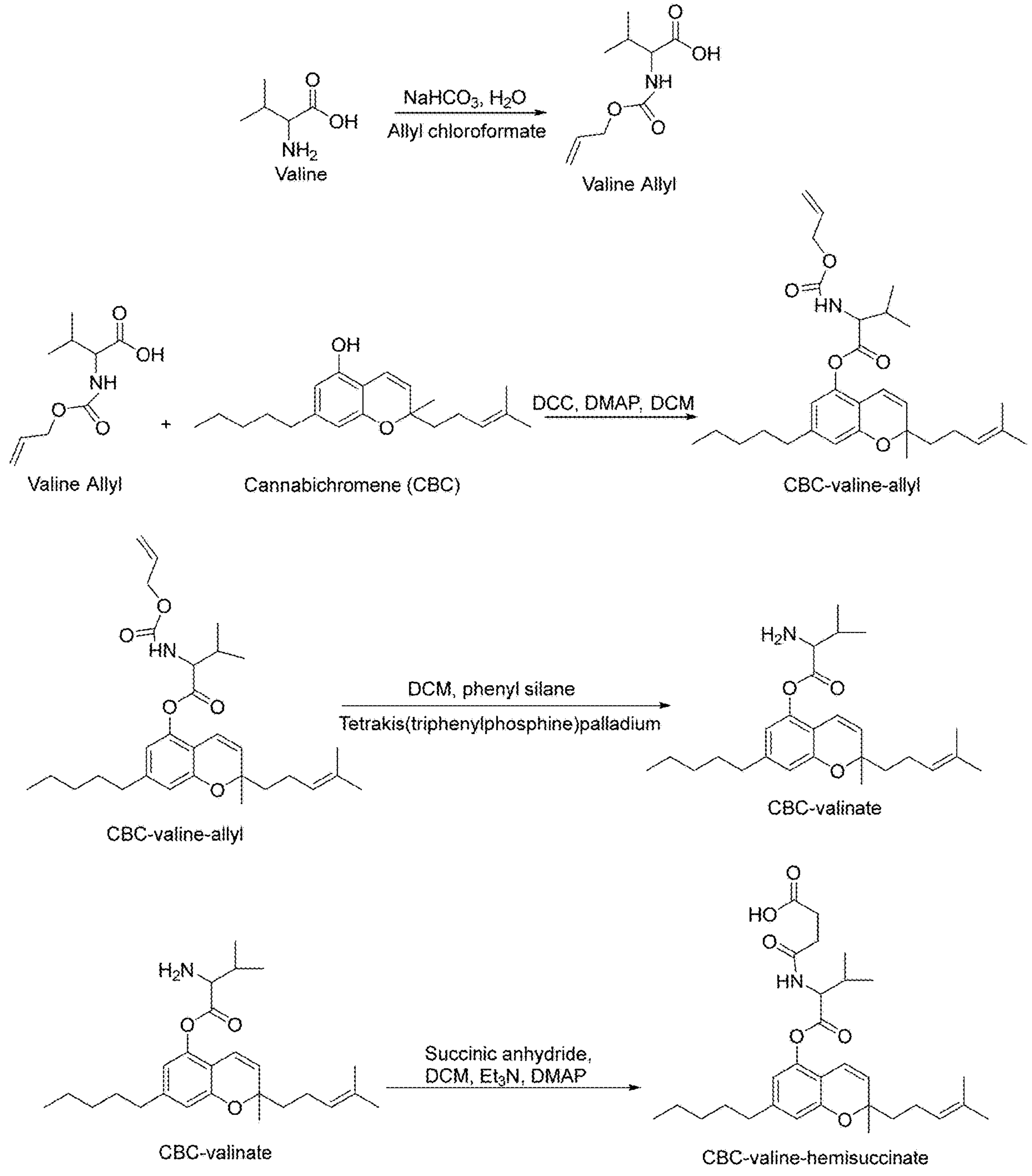
FIG. 1 provides an exemplary reaction scheme for making a cannabichromene derivative described herein.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a solvent" includes, but is not limited to, mixtures or combinations of two or more such solvents, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to conduct the methods of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "admixing" is defined as mixing two or more components together so that there is no chemical reaction or physical interaction. The term "admixing" also includes the chemical reaction or physical interaction between the two or more components.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as glaucoma. The effect can be therapeutic in terms of a partial or complete cure of a disease, condition, symptom or adverse effect attributed to the disease, disorder, or condition. The term "treatment" as used herein can include any treatment of glaucoma in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. In one aspect, "treating" and "treatment" includes an improved pharmacological and/or physiological effect when administered a compound described herein when compared to not administering the compound (i.e., the control).

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "acute pain" is pain that is not persistent, generally lasts a brief period of time (e.g., hours, 1-3 days, 1 week), and is resolved quickly. Examples of acute pain include, but are not limited to, acute pain of inflammation (including menstrual cramps, or dysmenorrhea), acute pain or stiffness of rheumatic or arthritic conditions ("flares" of osteoarthritis), minor pain of arthritis, acute joint and body pains, acute muscular aches and strains, acute pain of ligamentous sprains (including sprained ankle), acute backache, muscle soreness, minor aches and pains due to the common cold (including acute sore throat of infectious or non-infectious origin and sinus pain), minor aches and pains due to fever (including muscle achiness, or myalgia), acute headache (including acute tension-type and migraine), acute pain of minor surgery (including acute pain of dental extractions), acute toothache, occasional sleeplessness when associated with minor aches and pains, or any combination thereof.

The term "chronic pain" is pain that is persistent, generally lasts more than three months, up to years, and is not resolved quickly. An example of chronic pain includes pain caused by cancer or by metastases of cancer throughout the body, in particular, to bones. Other examples include chronic non-malignant pain, chronic neurologic diseases such as nerve impingement, spinal stenosis and other skeletal diseases of the back and limbs, chronic arthritis such as osteoarthritis, rheumatoid arthritis and psoriatic arthritis, chronic arthritis due to autoimmune diseases, fibromyalgia, etc.

The term "alkyl group" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

An alkyl group as used herein also refers to alkylene groups represented by the general formula $(CH_2)_n$, where n is an integer from 1 to 10. The alkylene group can be substituted or unsubstituted. For example, one or more of the hydrogen atoms of the alkylene group $(CH_2)_n$ can be substituted with another alkyl group such as, example, methyl, ethyl, propyl, isopropyl, butyl, and the like.

The term "aryl group" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl. Fused aryl groups including, but not limited to, indene and naphthalene groups are also contemplated.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a residue of an amino acid can be depicted by the structure below

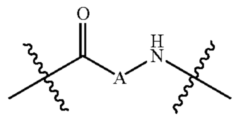

where A is the remaining portion of the amino acid molecule. For example, when the residue is of valine, A is

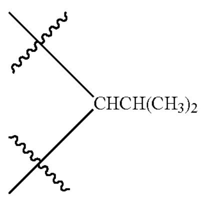

Unless otherwise specified, temperatures referred to herein are based on atmospheric pressure (i.e. one atmosphere).

Cannabichromene Derivatives and Methods for Making the Same

Described herein are new derivatives of cannabichromene that are effective in treating or preventing pain in a subject. The new cannabichromene derivatives have improved bioavailability, which enhances their ability to treat or prevent pain. In one aspect, the cannabichromene derivatives have the structure I or the pharmaceutically acceptable salt thereof

I

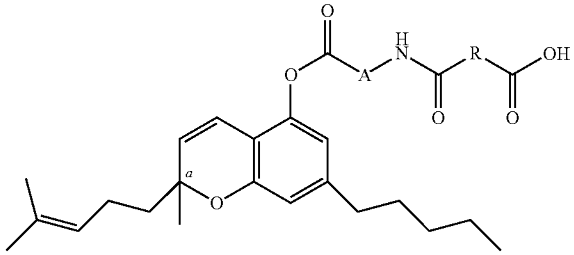

wherein

A is a residue of an amino acid or an alkyl group;

R is an alkyl group or an aryl group; and the stereochemistry at carbon a is substantially R, substantially S, or racemic.

In one aspect, the cannabichromene derivatives are produced by the process comprising:

(a) reacting cannabichromene with a protected amino acid to produce a protected amino ester;

(b) deprotecting the protected amino ester to produce the deprotected amino ester; and (c) reacting the deprotected amino ester with an anhydride.

The first step involves reacting the cannabichromene with a protected amino acid. In this aspect, the amino group is protected with a protecting group such as, for example, a tert-butyl BOC group. The reaction between the cannabichromene and the protected amino acid produces a protected amino ester. Deprotection of the protected amino ester yields the deprotected amino ester. An example of this reaction sequence is provided in FIG. 1, where CBC-valinate is the deprotected amino ester.

The deprotected amino ester is subsequently reacted with an anhydride. Examples of anhydrides useful herein include, but are not limited to, malonic anhydride, malic anhydride, glutaric anhydride, adipic anhydride, succinic anhydride, and phthalic anhydride. An example of this reaction sequence is provided in FIG. 1, where the deprotected amino ester CBC-valinate is reacted with succinic anhydride to produce CBC-valinate-hemisuccinate, which is cannabichromene derivative described herein.

In one aspect, the amino acid used to produce the cannabichromene derivatives described herein is any naturally occurring amino acid. The majority of amino acids possess a chiral center. Thus, when the amino acid reacts with cannabichromene, two diastereoisomers are produced. Referring to structure I above, the compound can be composed of two diastereoisomers, where with the first diastereoisomer, the stereochemistry at carbon a is R and with the second diastereoisomer, the stereochemistry at carbon a is S. The two diastereoisomers can be separated using techniques known in the art such as, for example, chromatography (reversed phase chromatography, HPLC) such that substantially pure forms of each diastereoisomer can be isolated. Thus, the stereochemistry at carbon a for each diastereoisomer is substantially R or S, where the term "substantially" refers to greater than 80%, greater than 85%, greater than 90%, greater than 95%, greater than 99%, or 100%. Examples of two diastereoisomers of a cannabichromene derivative described herein are provided below.

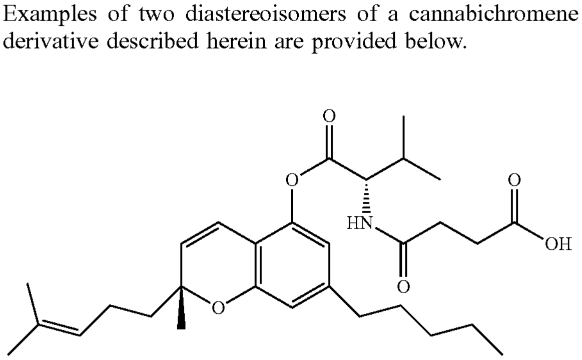

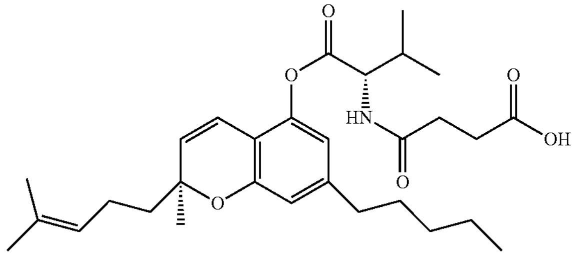

Pharmaceutical Compositions

In various aspects, the present disclosure relates to pharmaceutical compositions comprising a therapeutically effective amount of at least one cannabichromene derivative described herein, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one cannabichromene derivative described herein, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitoneally, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids that can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate,-phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate,-triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate,-dibutyrate,-dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl) imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multilayer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Methods for Treating or Preventing Pain

The cannabichromene derivatives described herein are effective in treating or preventing pain. The type and source of pain can vary. In one aspect, the pain is acute pain. In another aspect, the pain can be chronic pain. In other aspects, cannabichromene derivatives described herein can be administered to a subject prior to an event that will cause or produce pain (e.g., surgery, chemotherapy, etc.).

In one aspect, the cannabichromene derivatives described herein have significantly higher bioavailability when compared to cannabichromene (CBC). In one aspect, after administering the cannabichromene derivatives described herein to the subject, the peak concentration of the cannabichromene derivative is at least five times greater than the peak concentration of cannabichromene (CBC) administered at the same dose equivalent.

In another aspect, after administering the cannabichromene derivatives described herein to the subject, the peak concentration of the cannabichromene derivative is at least five times greater, at least six times greater, at least seven times greater, at least eight times greater, at least nine times greater, or about ten times the peak concentration of cannabichromene (CBC) administered at the same dose equivalent after one hour of administration. Although some of the cannabichromene derivative is metabolized to CBC, a majority of the cannabichromene derivatives will remain intact in circulation with greater bioavailability than naturally-occurring CBC. This in turn results in enhanced pain relief and prevention when the subject is administered the cannabichromene derivatives described herein.

The following examples are put forth so as to provide those of ordinary skill in the art with a complete disclosure and description of how the compounds, compositions, articles, devices and/or methods claimed herein are made and evaluated and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure.

ASPECTS

The present disclosure can be described in accordance with the following numbered aspects, which should not be confused with the claims.

Aspect 1. A compound having the structure I or the pharmaceutically acceptable salt thereof

I

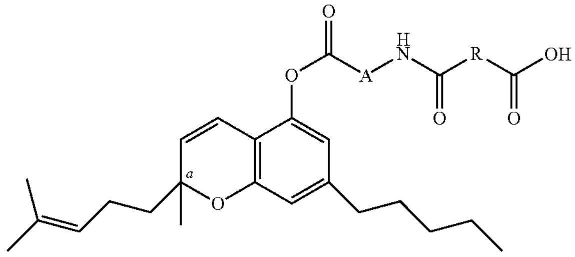

wherein

A is a residue of an amino acid or an alkyl group;

R is an alkyl group or an aryl group; and the stereochemistry at carbon a is substantially R, substantially S, or racemic.

Aspect 2. The compound of Aspect 1, wherein A is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine Aspect 3. The compound of Aspect 1, wherein is A valine.

Aspect 4. The compound of Aspect 1, wherein A is an alkyl group having 1 to 10 carbon atoms.

Aspect 5. The compound in any one of Aspects 1-3, wherein R is a $C_1$ to $C_{10}$ alky group.

Aspect 6. The compound in any one of Aspects 1-3, wherein R is $(CH_2)_n$, where n is an integer from 1 to 3.

Aspect 7. The compound of Aspect 6, wherein n is 2.

Aspect 8. The compound in any one of Aspects 1-7, wherein the stereochemistry at carbon a is racemic.

Aspect 9. The compound of Aspect 1, wherein the compound has the structure II

II

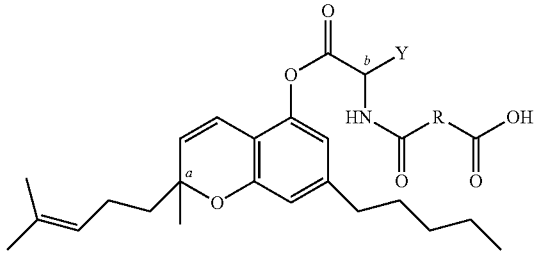

wherein Y is an alkyl group, and the stereochemistry at carbon b is substantially R, substantially S, or racemic.

Aspect 10. The compound of Aspect 8, wherein R is a $C_1$ to $C_{10}$ alky group and Y is $C_1$ to $C_{10}$ alky group.

Aspect 11. The compound of Aspect 8 or 9, wherein the stereochemistry at carbon a is substantially R or substantially S, and the stereochemistry at carbon b is substantially R or substantially S.

Aspect 12. The compound of Aspect 8 or 9, wherein the stereochemistry at carbon a is racemic.

Aspect 13. The compound of Aspect 1, wherein the compound has the structure III

III

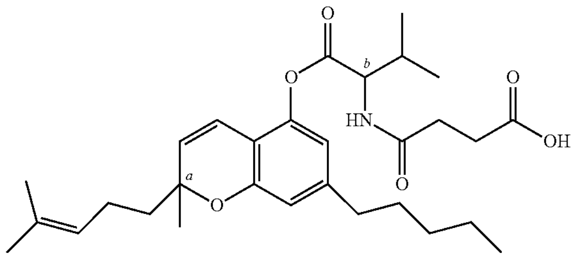

wherein the stereochemistry at carbon a is substantially R, substantially S, or racemic, and the stereochemistry at carbon b is substantially R or substantially S.

Aspect 14. The compound of Aspect 3, wherein the stereochemistry at carbon a is racemic.

Aspect 15. The compound in any one of Aspects 1-14, wherein the compound is produced by the process comprising:

reacting cannabichromene with a protected amino acid to produce a protected amino ester;

deprotecting the protected amino ester to produce the deprotected amino ester; and reacting the deprotected amino ester with an anhydride.

Aspect 16. The compound of Aspect 15, wherein after step (c), when two diastereoisomers are produced, separating the two diastereoisomers from each other.

Aspect 17. A pharmaceutical composition comprising the compound in any one of Aspects 1 to 16 and a pharmaceutically acceptable carrier.

Aspect 18. A method for treating or preventing pain in a subject in need thereof comprising administering to the subject the compound in any one of Aspects 1 to 16 or the composition of Aspect 17.

Aspect 19. The method of Aspect 18, wherein the patient is experiencing acute or chronic pain.

Aspect 20. The method of Aspect 18, wherein the patient is experiencing pain caused by a chemotherapeutic agent.

Aspect 21. The method in any one of Aspects 18 to 20, wherein the compound or composition is administered orally or parenterally.

Aspect 22. The method in any one of Aspects 18 to 21, wherein after administering the compound or composition to the subject, the peak concentration of the compound is at least five times greater than the peak concentration of cannabichromene (CBC) administered at the same dose equivalent.

EXAMPLES

Methods

Drugs

Following the general procedure outlined in FIG. 1, where compound 1 is valine, CBC-valinate (CBC-Val) was synthesized to test the validity of the synthetic protocol. Valine (5 g) was dissolved in 34 mL of distilled water and 5.8 gram of sodium carbonate was added in several portions. Allyl chloroformate (10 mL) was added at once after the bubbling stopped. The solution was stirred for 24 hours at 22° C. Concentrated hydrochloric acid was then used to adjust the pH to 1. The solution was extracted with ethyl acetate 8 times and the organic layer was rinsed with brine and dried over sodium sulfate. The solvent was evaporated to dryness to give 6.5 g of the crude product as colorless syrup.

A 1.1 equivalent of this product was dissolved in dichloromethane and 1.1 equivalent of DCC was added to it (solution A). CBC (1 equivalent) was dissolved in dichloromethane along with a catalytic amount of DMAP (dimethyl amino pyridine) which was added drop-wise to solution A. The reaction mixture was stirred at room temperature for 1 hour and the reaction progress was monitored through TLC. After one hour the reaction mixture was worked up and the product was purified using silica gel column chromatography. Fractions having the product were combined and evaporated to obtain the protected CBC-valine ester (95% yield). The latter was dissolved in dichloromethane and 0.05 mmol of tetrakis(triphenylphosphine) palladium was added along with 0.01 mmol of phenyl silane. The reaction was allowed to stir at room temperature for 30 minutes. The solvent was then evaporated and the product 6 was purified using column chromatography (>85% yield). The structure of product 6 was confirmed by spectral analysis ($^{1}$H-NMR and $^{13}$C-NMR).

CBC and CBC-val-HS were dissolved in a solution of 10% ethanol/10% cremophore and 80% saline. Mice received IP injection of test compounds in a volume of 1.0 ml/kg for the abdominal writhing assay and 1.0 ml/kg, IP in the hot plate assay. For pharmacokinetic studies, drug was given in a volume of 1.0 ml/kg for tail vein and oral gavage administration. CBC-val-HS doses were calculated to be the dose equivalent of CBC.

Animals

All experimental procedures were approved by the University of Mississippi Institutional Animal Care and Use Committee (Protocol #19-009). Animal studies reported in compliance with the ARRIVE guidelines. Male wild-type $C_{57}$BL/6 mice (7-10 weeks, 17-30 grams) were used for all behavioral studies and Male CD-1 (6-7 weeks, 20-25 grams) were used for all pharmacokinetic studies. Mice were purchased from Envigo, (Indianapolis, IN, USA) and acclimated for one week prior to experimentation. Mice were group-housed (n=4-5) in a polycarbonate tub with soft bedding in a temperature (22°±2) and humidity-controlled vivarium under a normal 12:12 h light/dark cycle (lights on at 06:00) with food and water ad libitum. Behavioral testing was performed during the hours of 08:00-18:00 with 30-minute acclimation to the testing room for all studies. Mice were assigned treatments through random block assignment per cage and experimenters were blinded to treatment conditions. Equipment was thoroughly sanitized with 70% ethanol between mice.

Hot Plate

The hot plate (Harvard Instruments, Model #52-8570) was used to quantify thermal nociception. This consisted of an open top acrylic enclosure (12.7×15.24 cm) positioned on a plate heated set to 52° C. Test compounds were administered IP 30 minutes prior to behavioral testing. Mice were placed onto the hot plate and immediately removed following a nociceptive response (i.e., hind paw flutter, hind paw lick, or an escape response). A 45 second cut-off was used to prevent tissue damage. The latency of a withdrawal response served as the dependent measure.

Abdominal Writhing

Abdominal writhing testing was used to quantify inflammatory nociception. Testing was conducted in clear, open-top, acrylic observation chambers (12.7×15.24 cm) located on a smooth surface. Test compounds were administered IP 30 minutes prior to behavioral testing. For testing, mice were then given an IP injection of 0.7% acetic acid in a volume of 10.0 ml/1 kg and immediately placed in an observation chamber for 30-minute test. The number of abdominal writhes served as the dependent measure.

Pharmacokinetic Study

A pharmacokinetic study of CBC and CBC-val-HS was conducted using either intraperitoneal (IP), oral gavage, or and intravenous (IV; lateral tail vein) administration routes. For each route, four to five subjects were sacrificed at 0, 0.05, 0.25, 0.5, 1, 2, 4, 8, and 24 hr after drug administration. Mice were anesthetized with isoflurane, and whole blood was collected by cardiac puncture. Plasma was isolated by centrifugation (2000 rpm, 5 min) and stored at −80° C. until assayed.

For CBC in the plasma samples were extracted using solid phase cartridges. CBC-VHS plasma samples were diluted with cold acetonitrile, sonicated, centrifuged, transferred supernatant to another extraction tube, evaporated the solvent and reconstituted with acetonitrile for the analysis. The LC-MS-MS system consists of a Shimadzu Prominence UHPLC with a dual pump, a vacuum solvent micro-degasser, a controlled-temperature auto-sampler, and an MS-MS detector (Applied Biosystems/MSD Sciex QTRAP 4500/3200 with a turbo-ion ESI source operating the positive-ion multiple reaction monitoring, or MRM, mode). The LC system uses a reversed-phase C-18 column to separate the different analytes. Multiple reaction monitoring (MRM) was utilized for detecting specific MS-MS transitions for each analyte and its internal standard (I.S.). Deuterated internal standard D3-CBC was used for the quantitation of CBC and CBCVHS. The peak area corresponding to each extracted MRM was measured and correlated to a multiple point calibration curve to determine the plasma concentration of each analyte. The LC/MS/MS system is controlled by Analyst® 1.6.3 software.

Results

Cannabichromene (CBC) exerts anti-nociceptive and analgesic effects in a number of rodent models of pain. A novel derivative of CBC, cannabichromene-valinate-hemisuccinate (CBC-Val-HS) was developed to improve the bioavailability of CBC. The synthesis of CBC-Val-HS is provided in FIG. 1, with spectroscopic characterization provided in FIGS. 5-29.

While the structure of CBC-Val-HS might appear to be that of a prodrug, it was discovered to be a true derivative and not a typical prodrug. When CBC-Val-HS is administered to animals, parenterally or orally, the major chemical component detected in the circulating plasma is the intact CBC-Val-HS, with free CBC representing a small fraction relative to the intact CBC-Val-HS. Furthermore, the oral bioavailability of CBC-Val-HS is approximately three times that of CBC itself.

The metabolic parameters of CBC-Val-HS are unique compared to other cannabinoid-based chemical entities. Unlike THC-Val-HS, which is not found in plasma after parenteral administration (therefore a true prodrug) and unlike CBD-Val-HS, which is the only entity found in the plasma with no significant level of CBD (therefore not a prodrug at all and levels of CBD are only seen in the tissues), CBC-Val-HS is a partial prodrug, where about one-third of the derivative is observed in the plasma as the free CBC and the other two-thirds as the intact CBC-Val-HS. Therefore, CBC-Val-HS is distinctly different than the same derivative of the other two cannabinoids.

Figure 2:
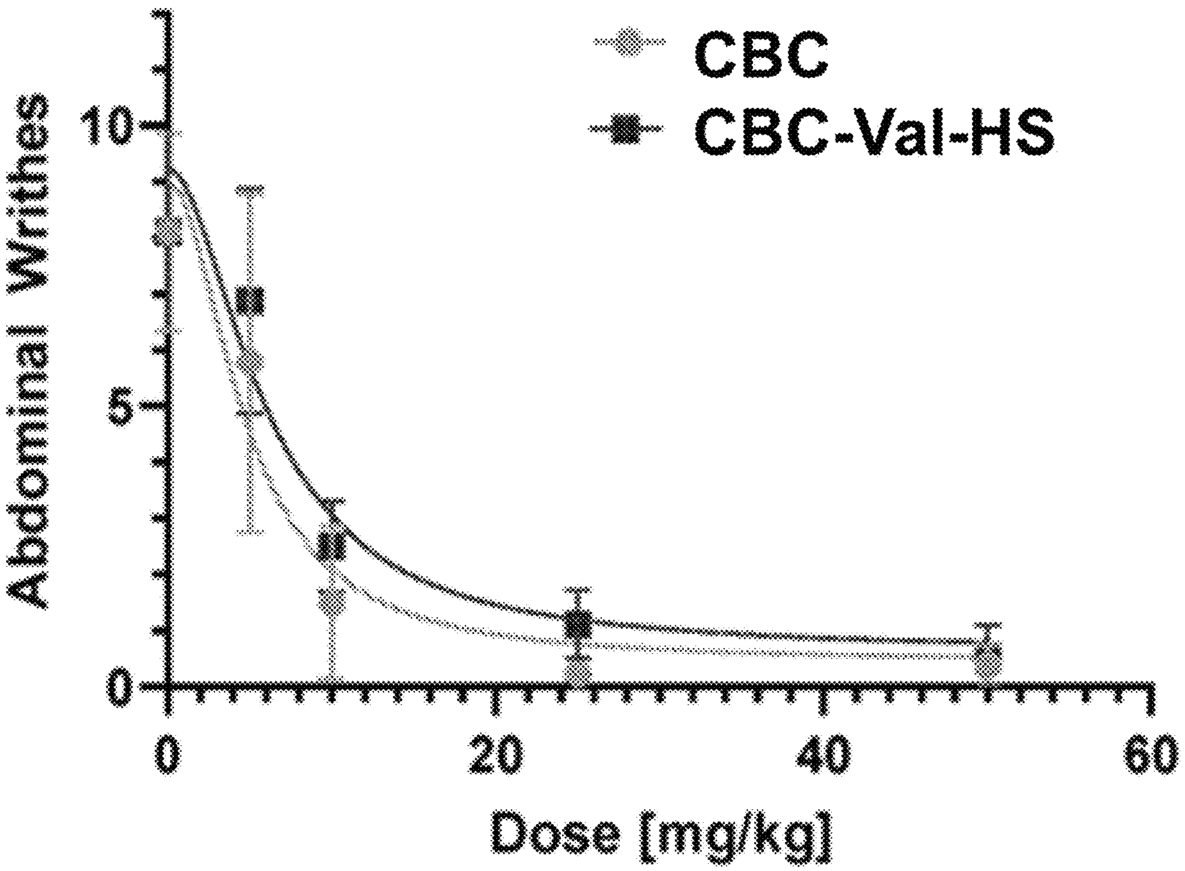
FIG. 2 shows the efficacy and potency of CBC-Val-HS against acute pain/nociception was assessed in the mouse abdominal writhing test

The efficacy and potency of CBC-Val-HS against acute pain/nociception was assessed in the mouse abdominal writhing test. Intraperitoneal administration of 0.07% acetic acid resulted in a significant number of abdominal writhes. When increasing doses of CBC-Val-HS were administered 30 minutes prior to acetic acid injection, the number of acid-induced writhes significantly decreased, indicating anti-nociceptive activity against acute inflammatory pain (Two-way ANOVA, post-hoc Holm Sidek multiple comparisons). Results are provided in FIG. 2. No differences in overall efficacy or potency were noted in comparison to naturally-occurring CBC, as the main statistical effects were restricted a factor of dose ($F=60.12$, $p<0.001$) and not drug ($F=1.62$, $p=0.38$).

Figure 3A:
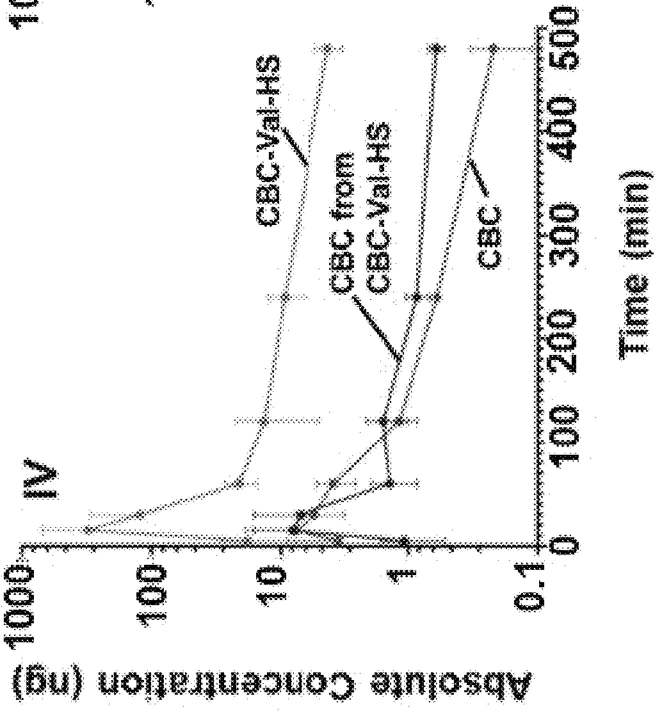
FIGS. 3A-3B shows the bioavailability of CBC-Val-HS was significantly enhanced over CBC via intravenous (A) and oral (B) administration.
Figure 3B:
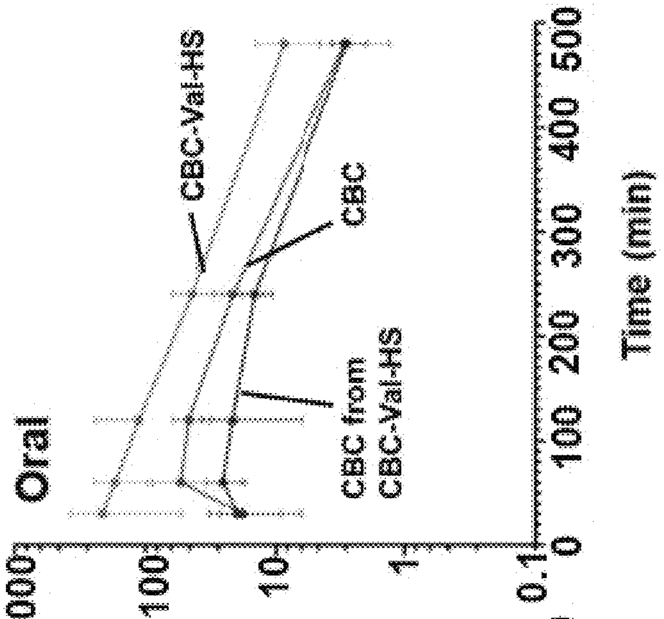

While CBC-Val-HS and CBC were equally efficacious against acute pain/nociception, the bioavailability of CBC-Val-HS was significantly enhanced over CBC. To assess this, CBC-Val-HS and CBC were each administered to mice through three routes: oral gavage, intravenous injection, or intraperitoneal injection. Blood samples were isolated from the mice in the minutes and hours following administration to determine availability of the parent compounds and any metabolites. Analysis of test compounds within the serum revealed that the peak concentration of CBC-Val-HS was greater than 10× higher in the hour following intravenous administration than the peak concentration of CBC administered at the same dose equivalent. Some CBC-Val-HS was metabolized to CBC, and the availability of this metabolized CBC overlapped with that observed in mice treated with CBC alone. Therefore, while some CBC-Val-HS is metabolized to CBC, a majority of CBC-Val-HS remained intact in circulation with greater bioavailability than naturally-occurring CBC. While not as pronounced, oral administration of CBC-Val-HS also resulted in significantly greater bioavailability than CBC. Results are provided in FIGS. 3A-3B.

Figure 4A:
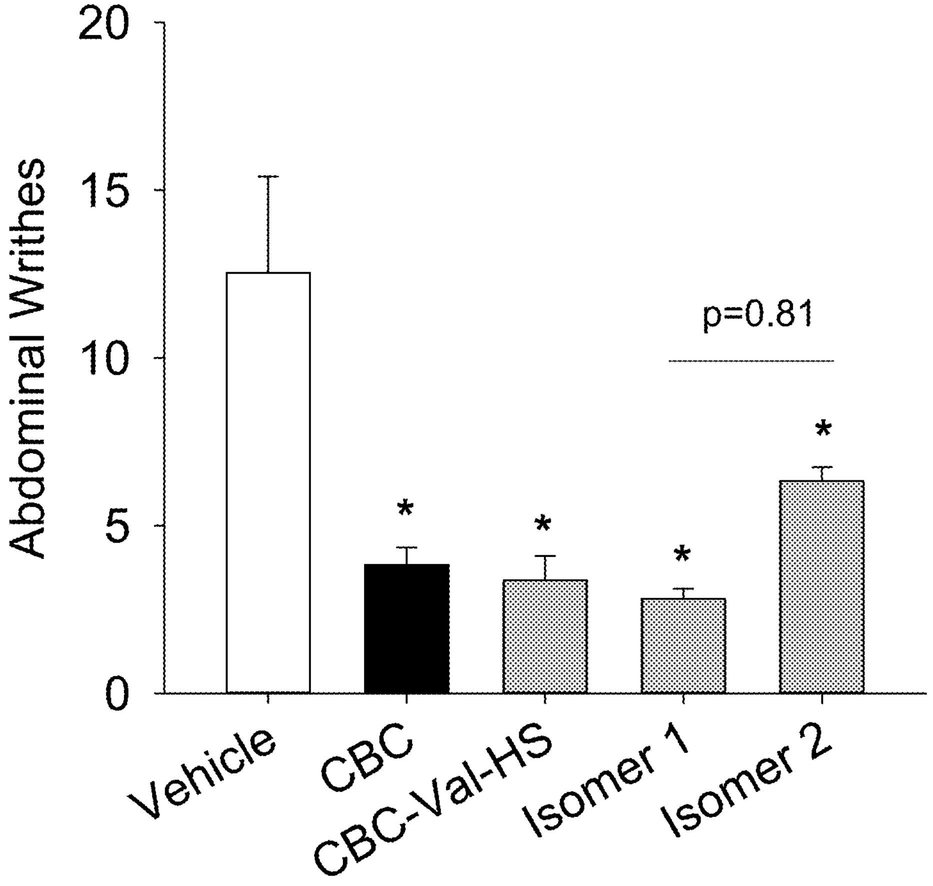
FIGS. 4A-4B show the number of abdominal writhes (A) and latency to hotplate withdrawals (B) in mice when administered CBC-Val-HS in racemic form and two diastereoisomers when compared to vehicle and CBC.
Figure 4B:
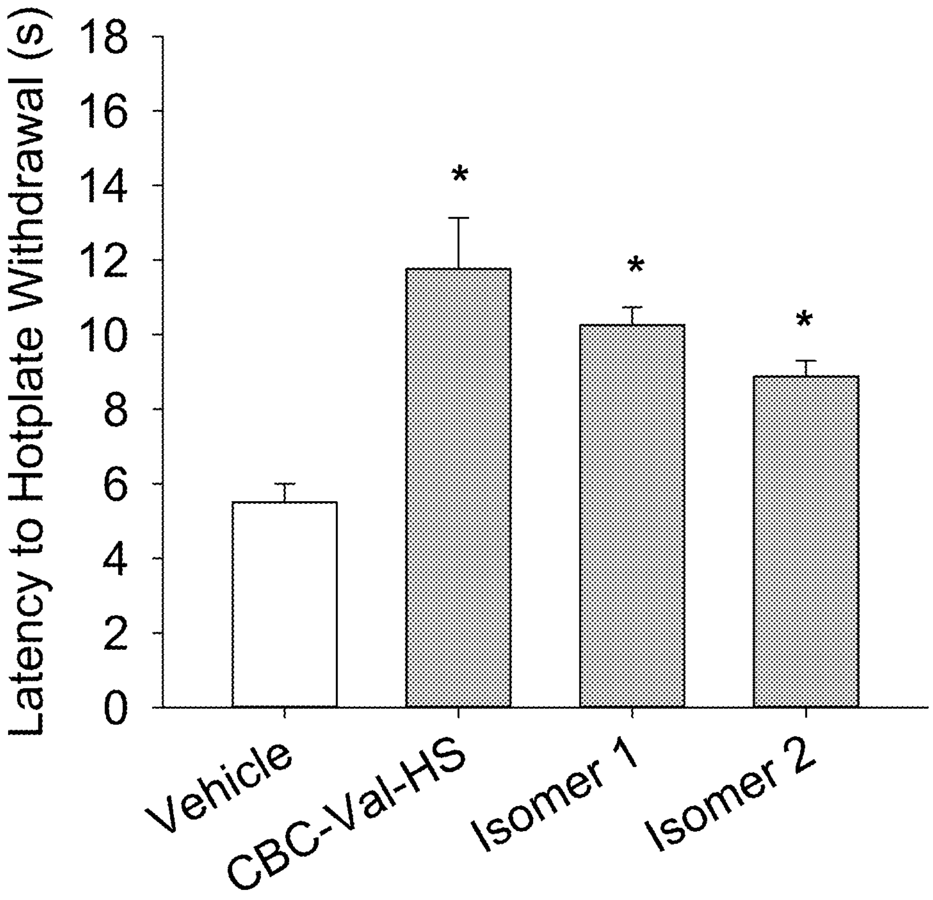
Figure 5:
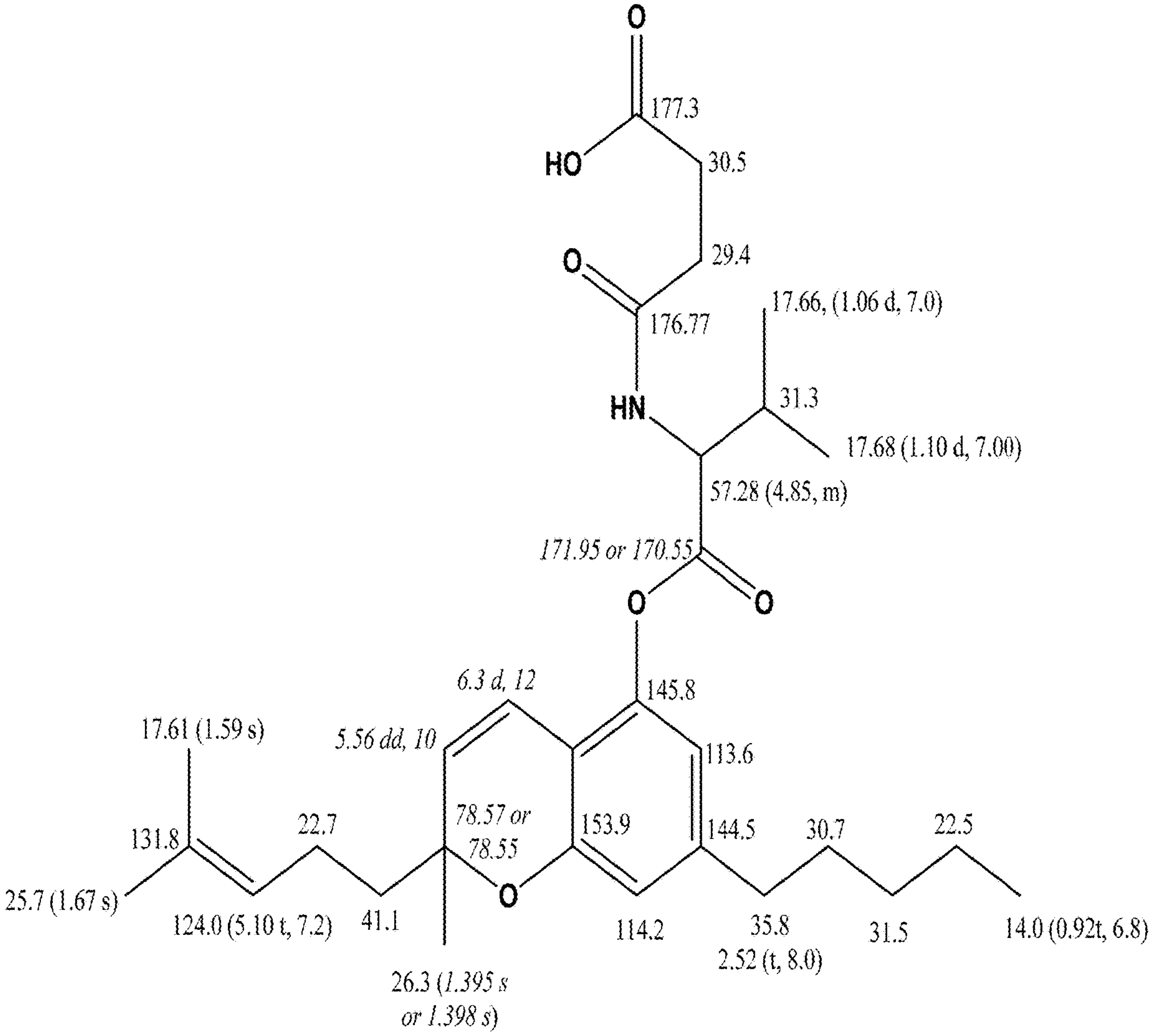
FIGS. 5-29 provide spectroscopic characterization of CBC-Val-HS.
Figure 6:
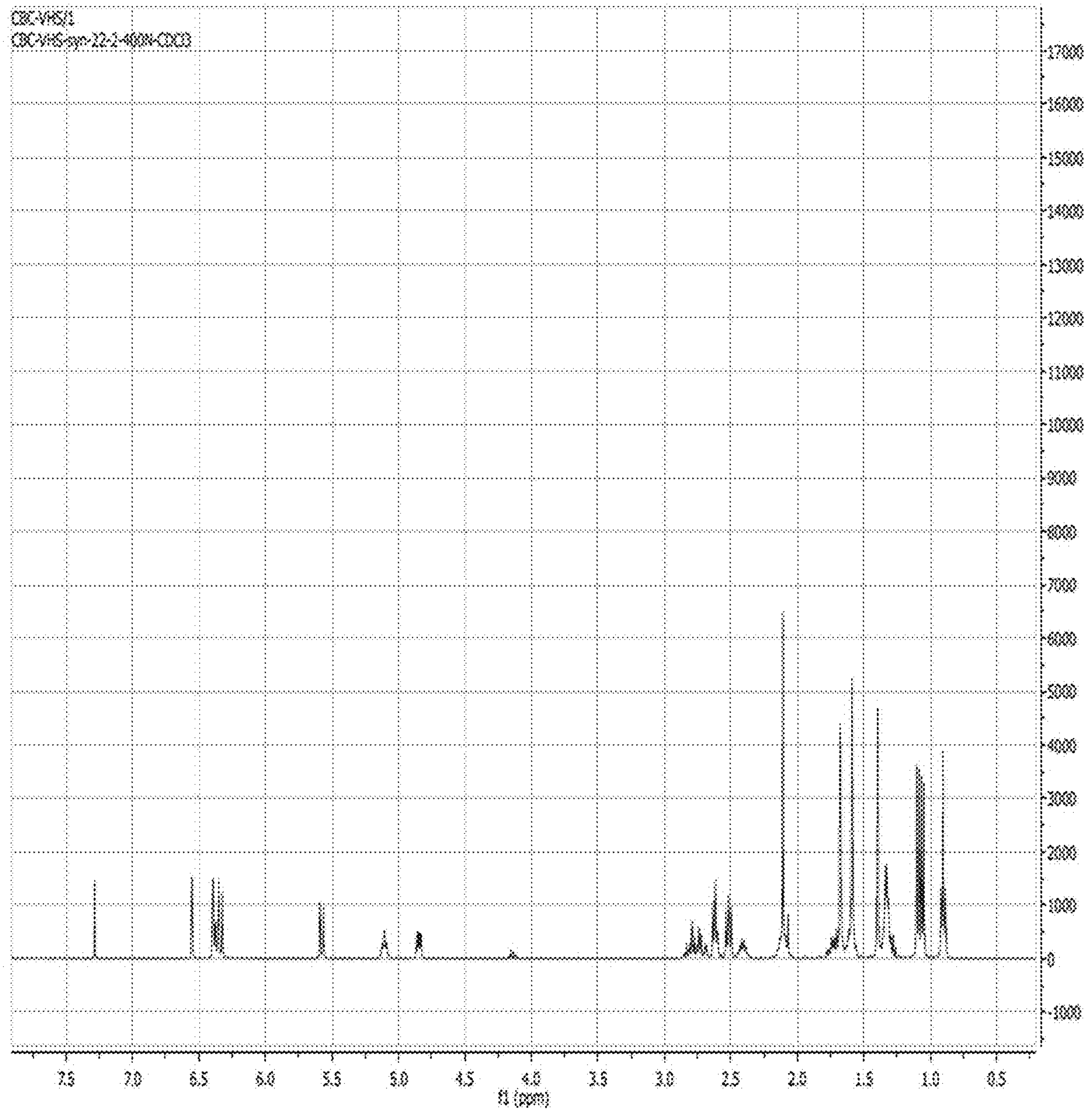
Figure 7:
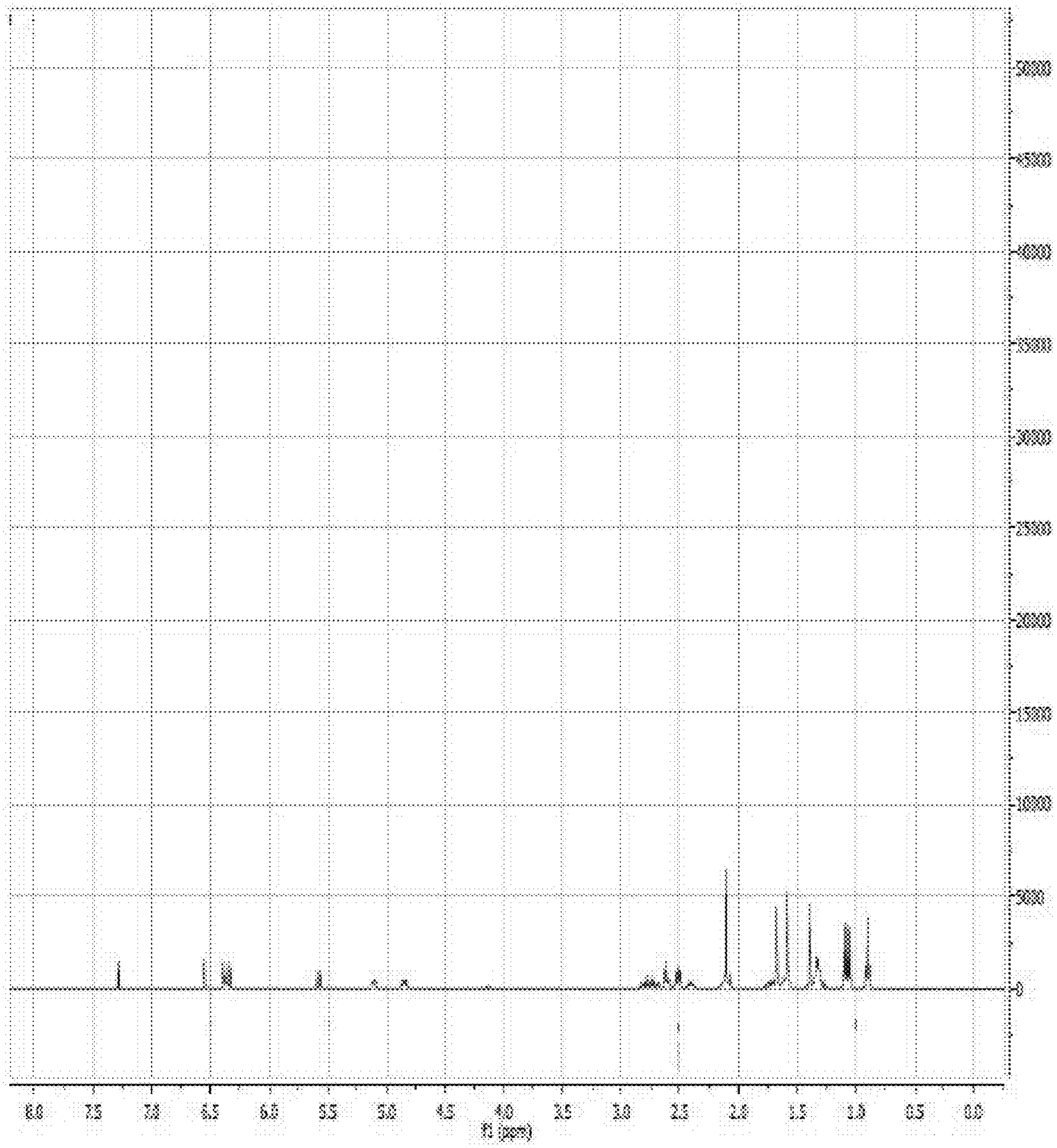
Figure 8:
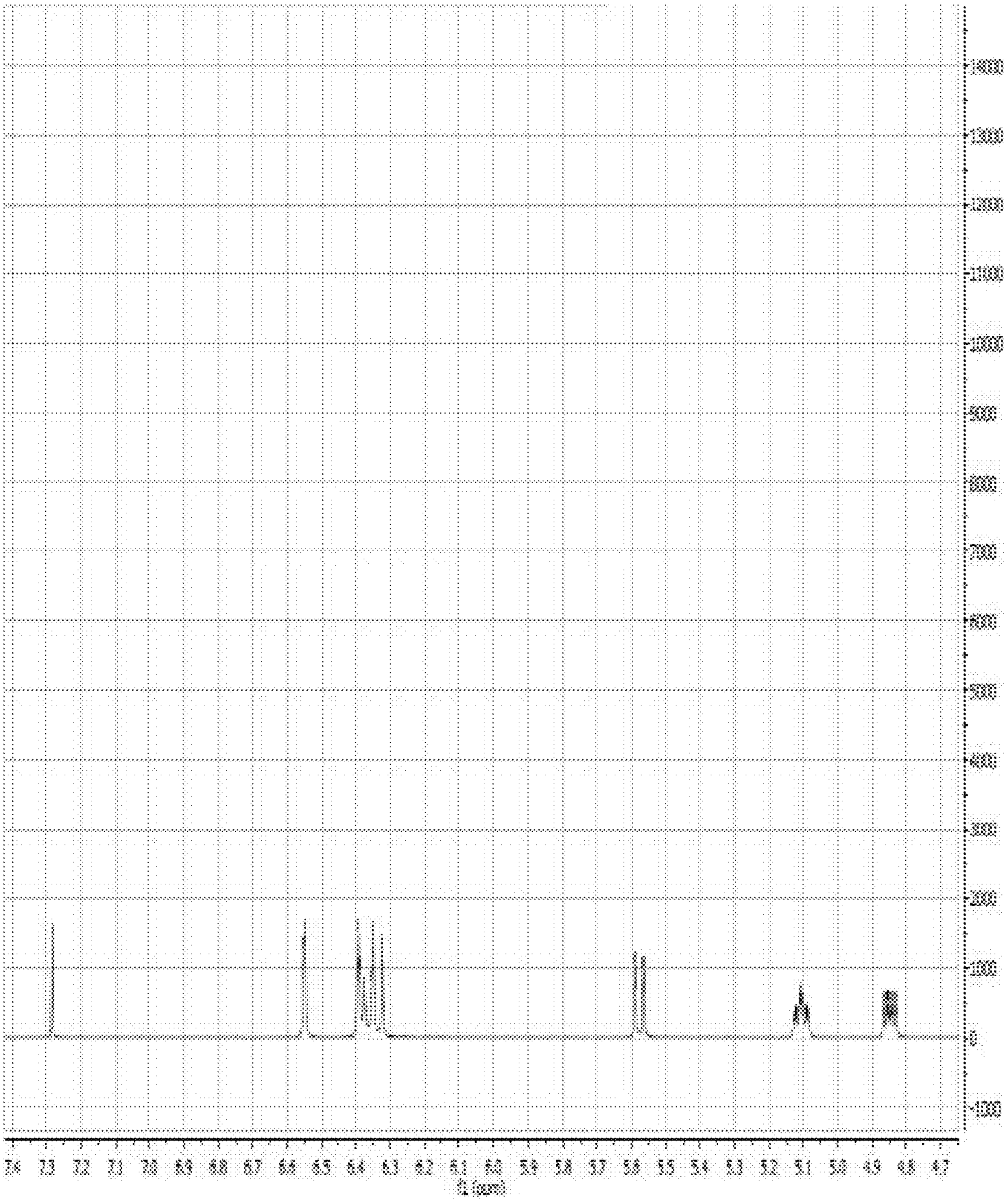
Figure 9:
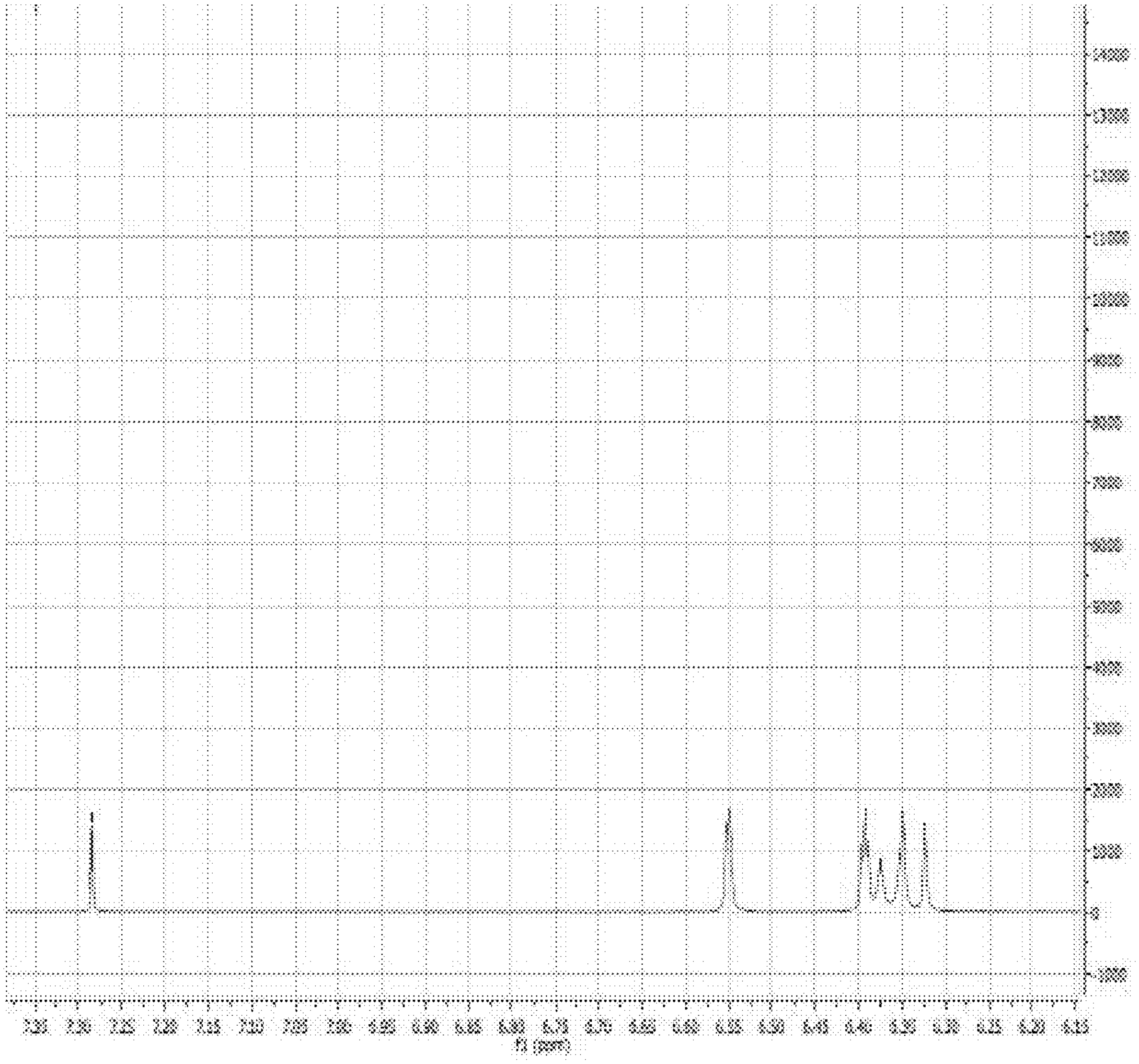
Figure 10:
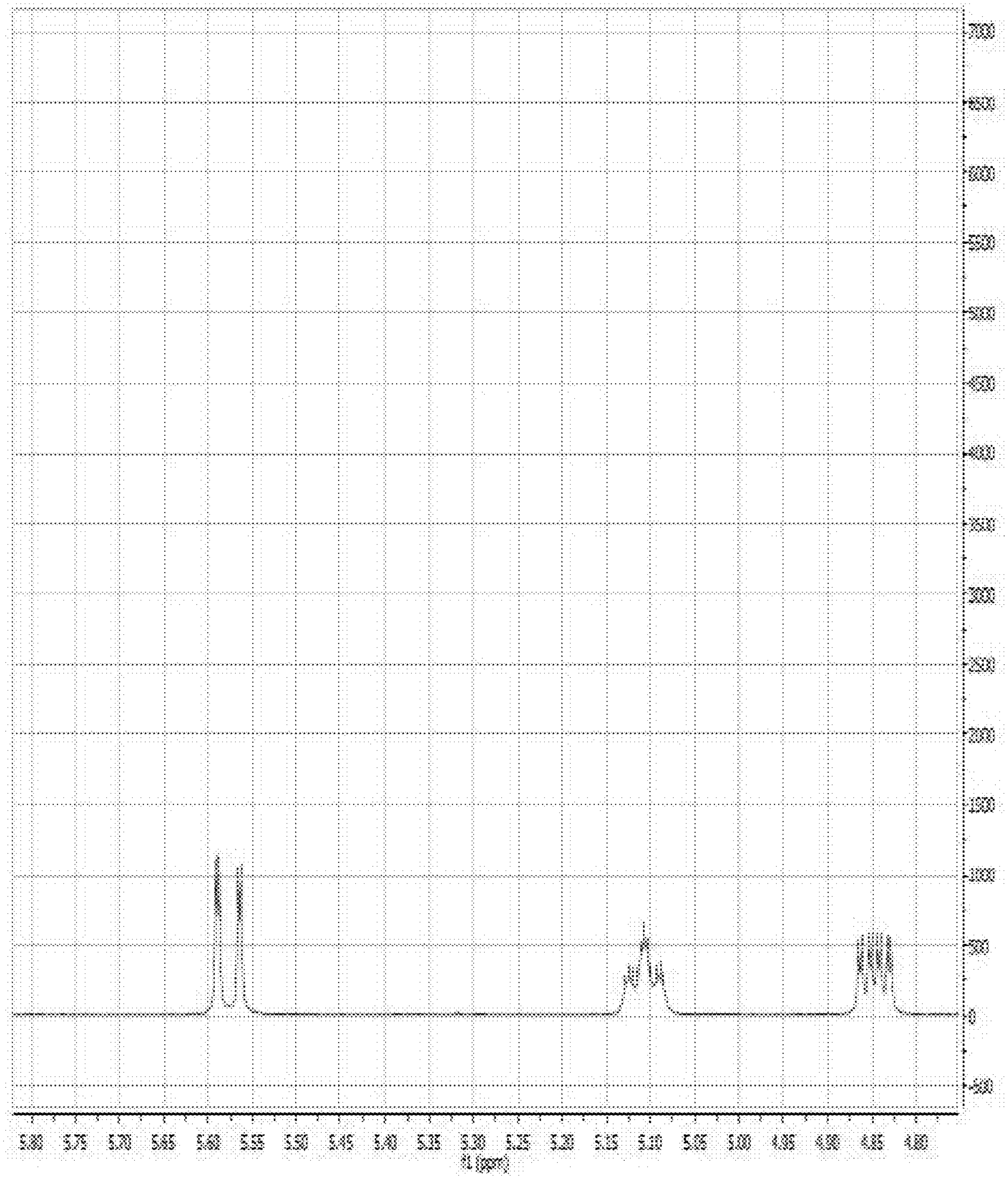
Figure 11:
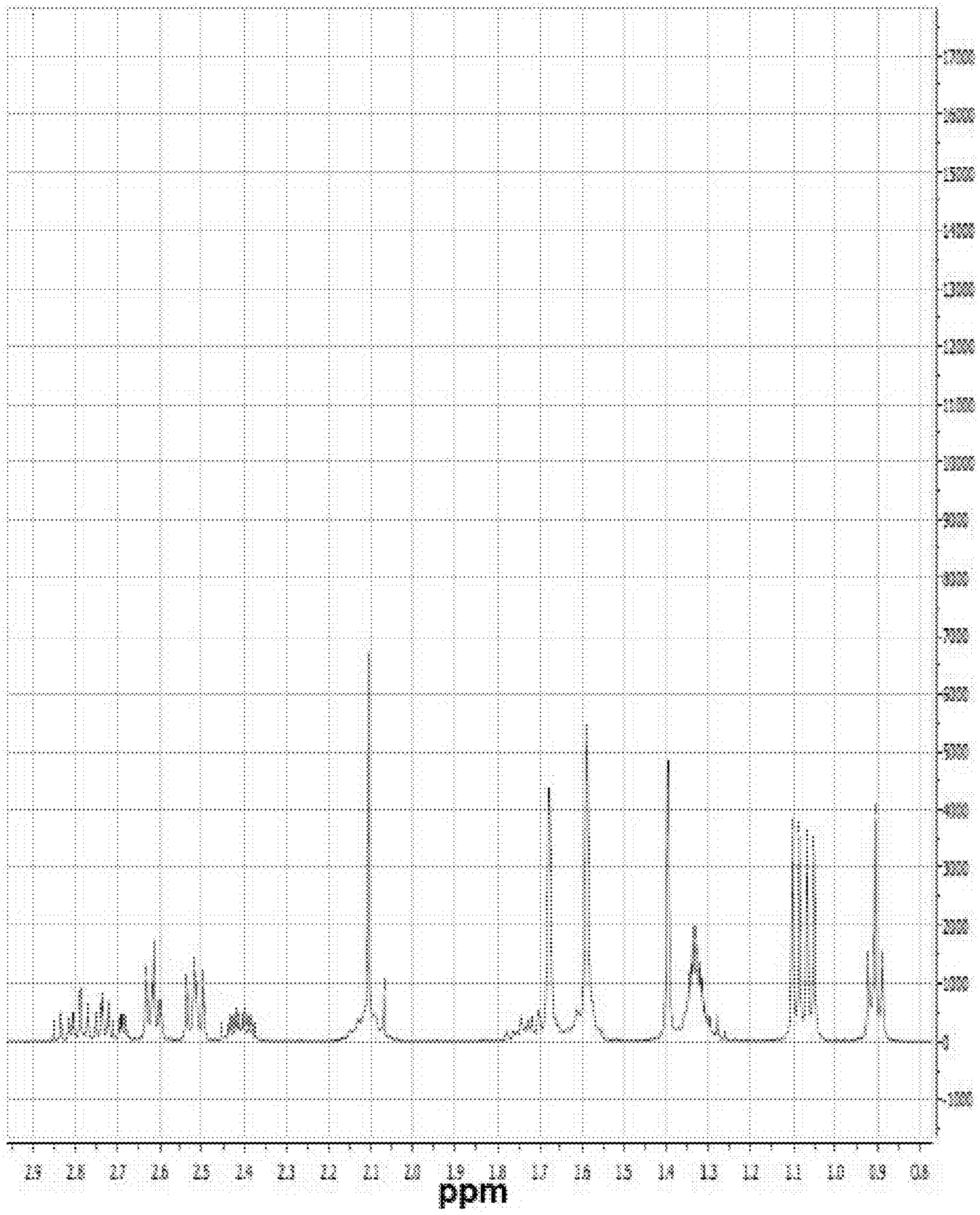
Figure 12:
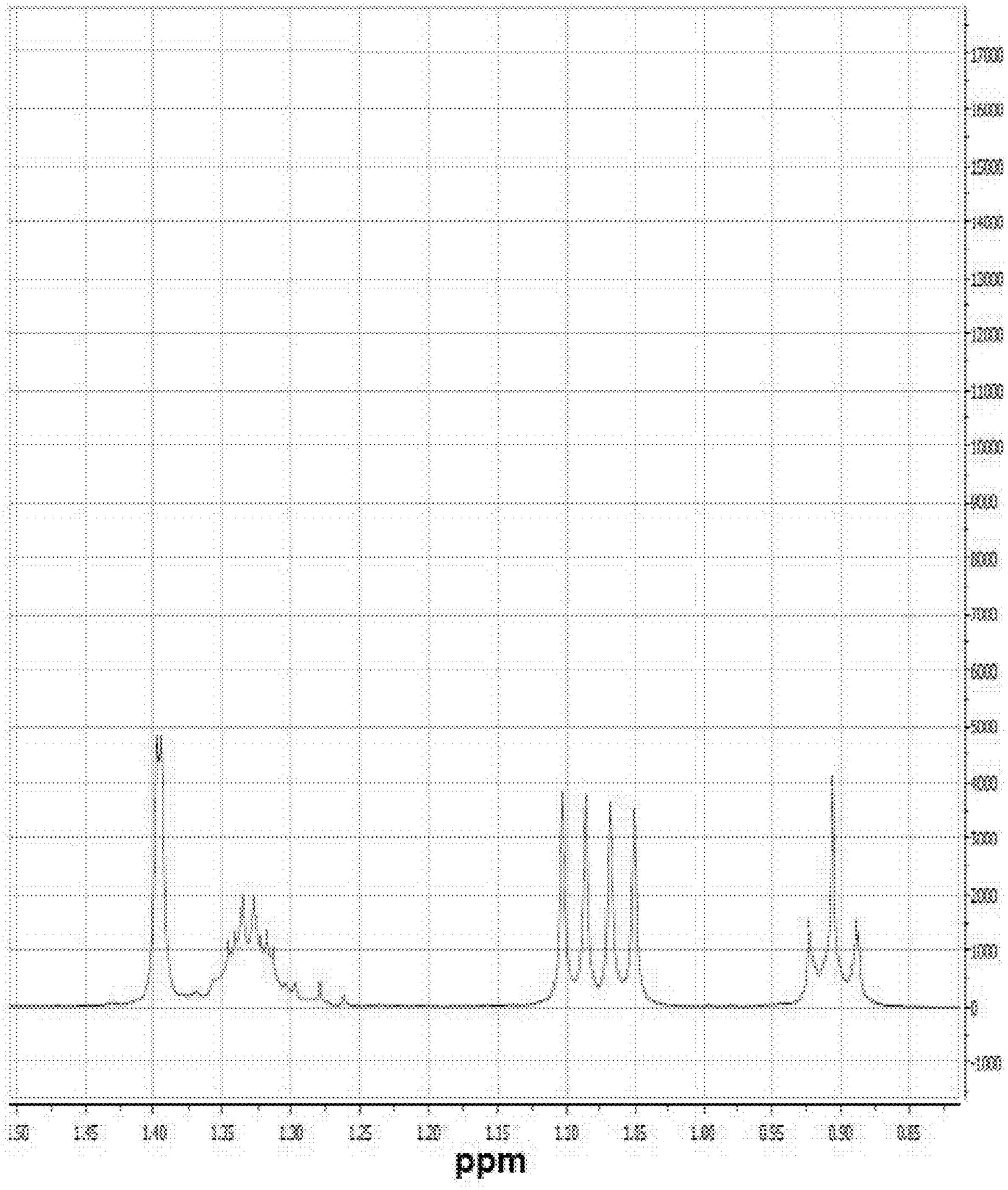
Figure 13:
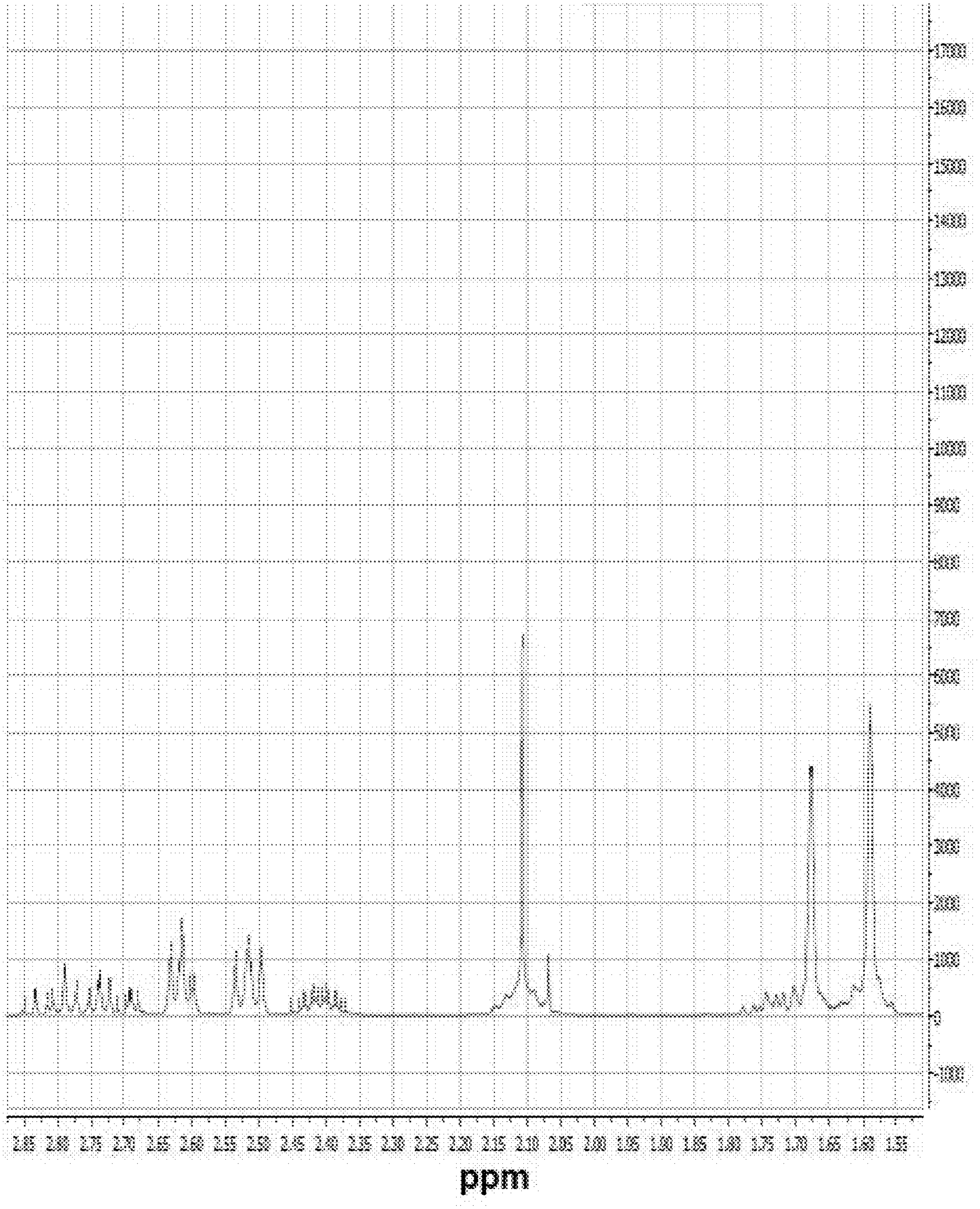
Figure 14:
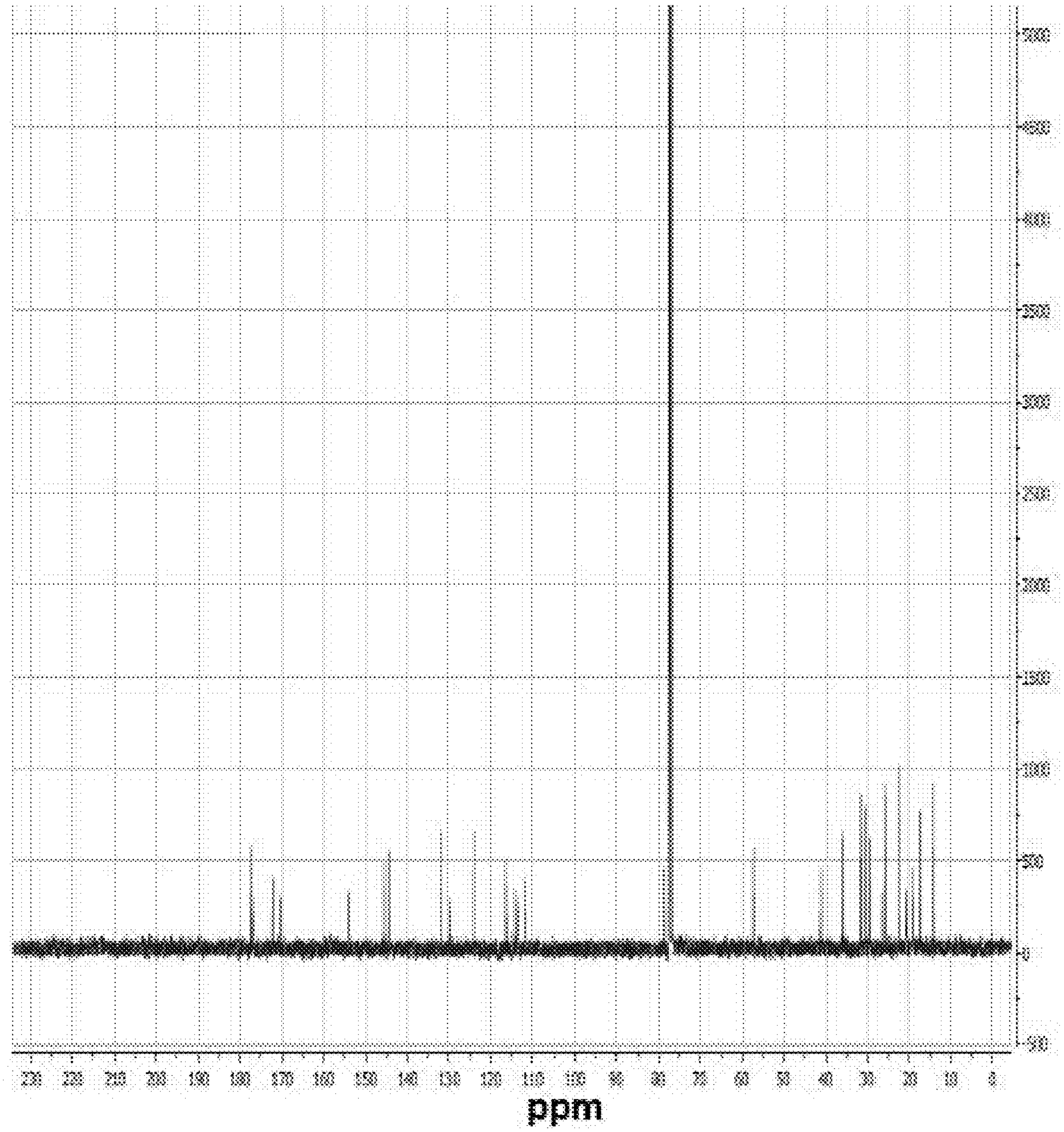
Figure 15:
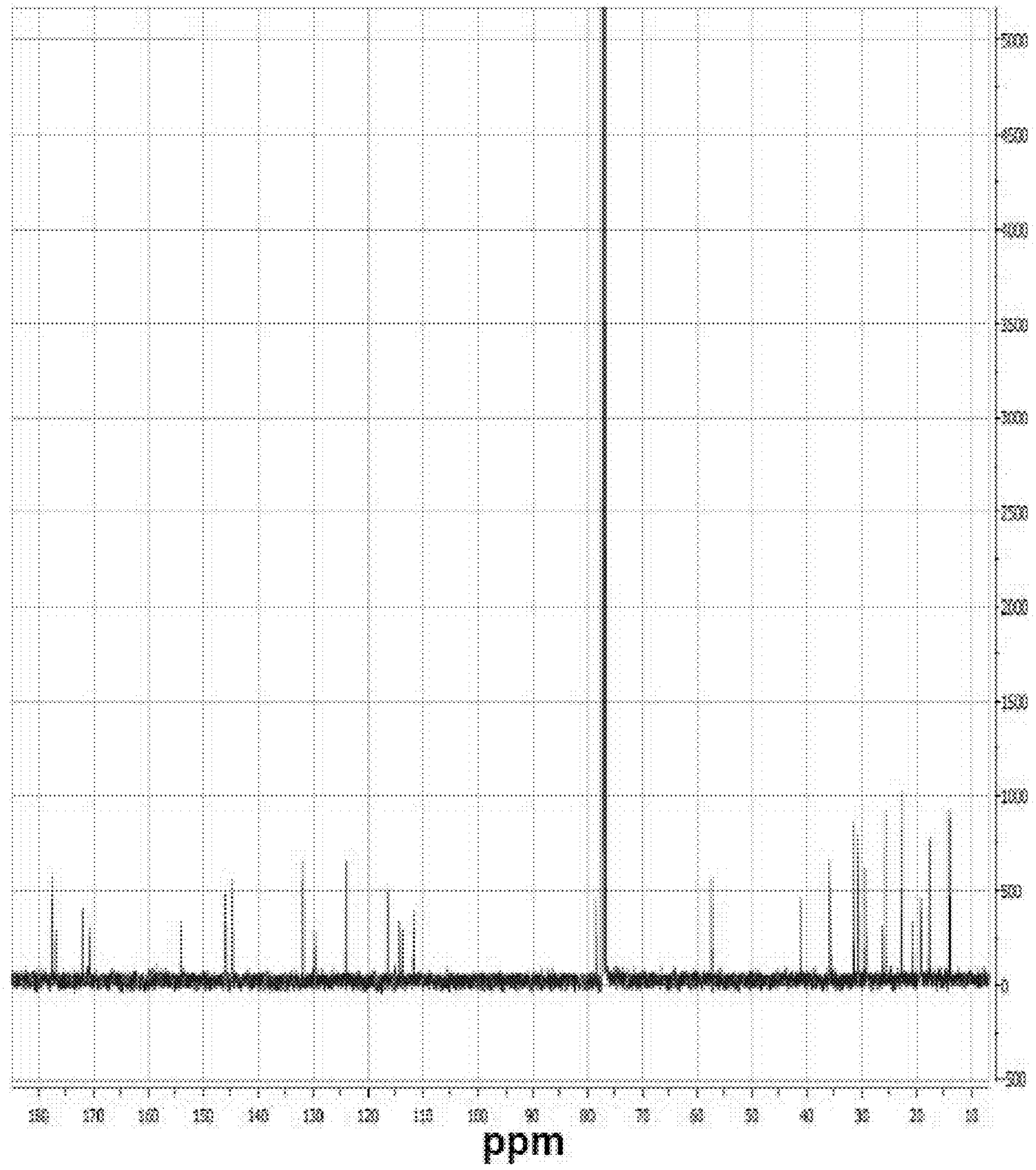
Figure 16:
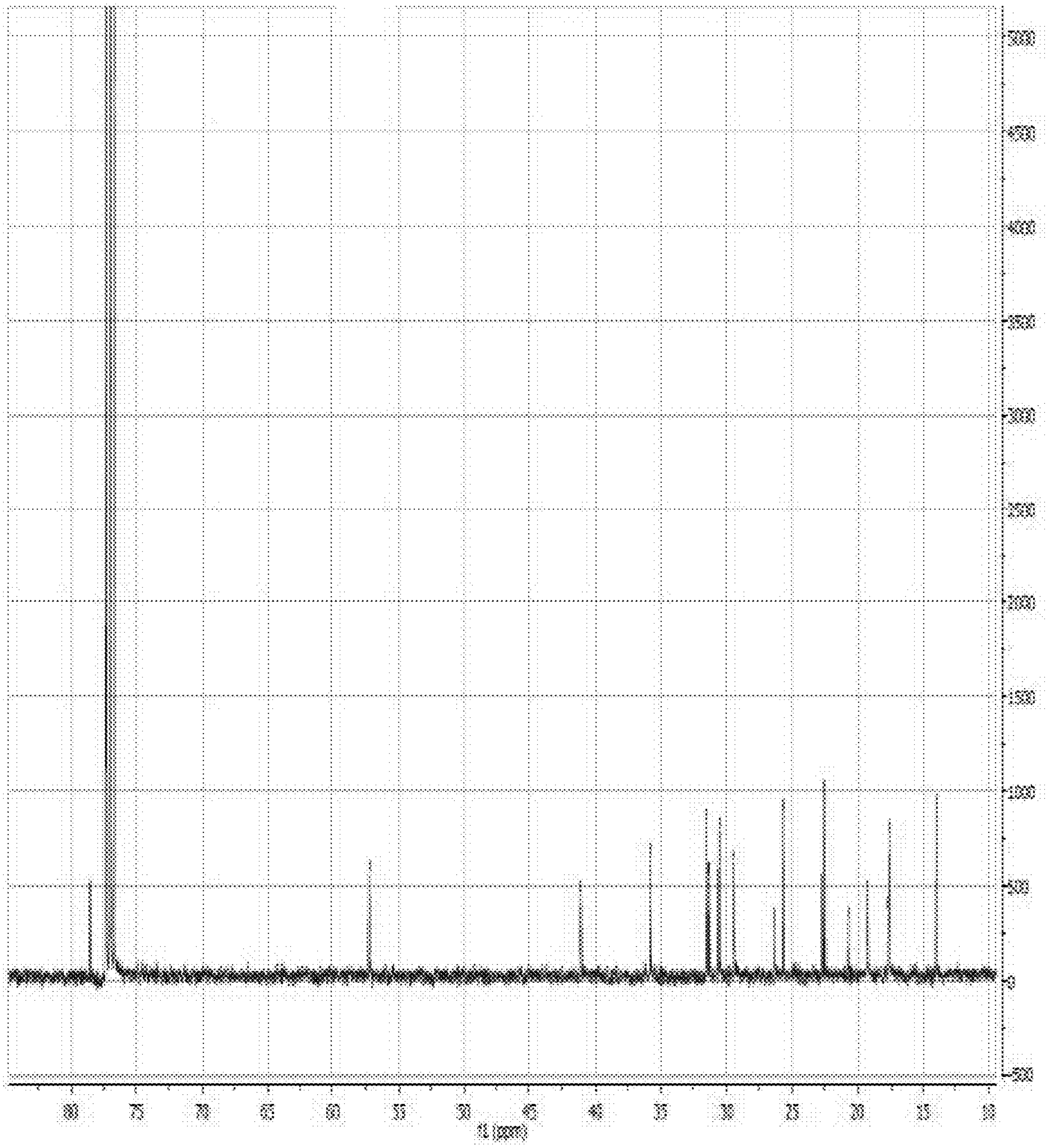
Figure 17:
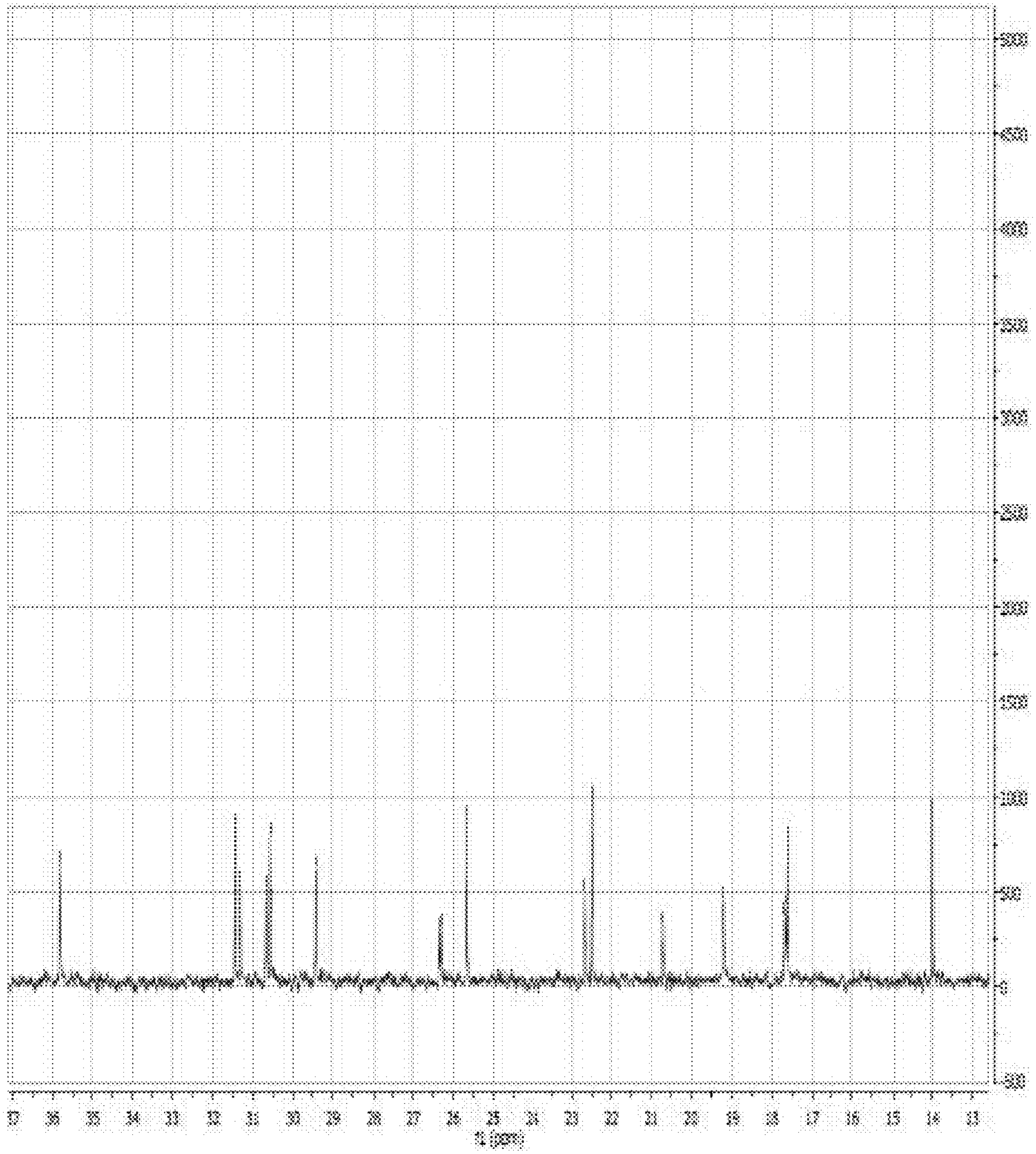
Figure 18:
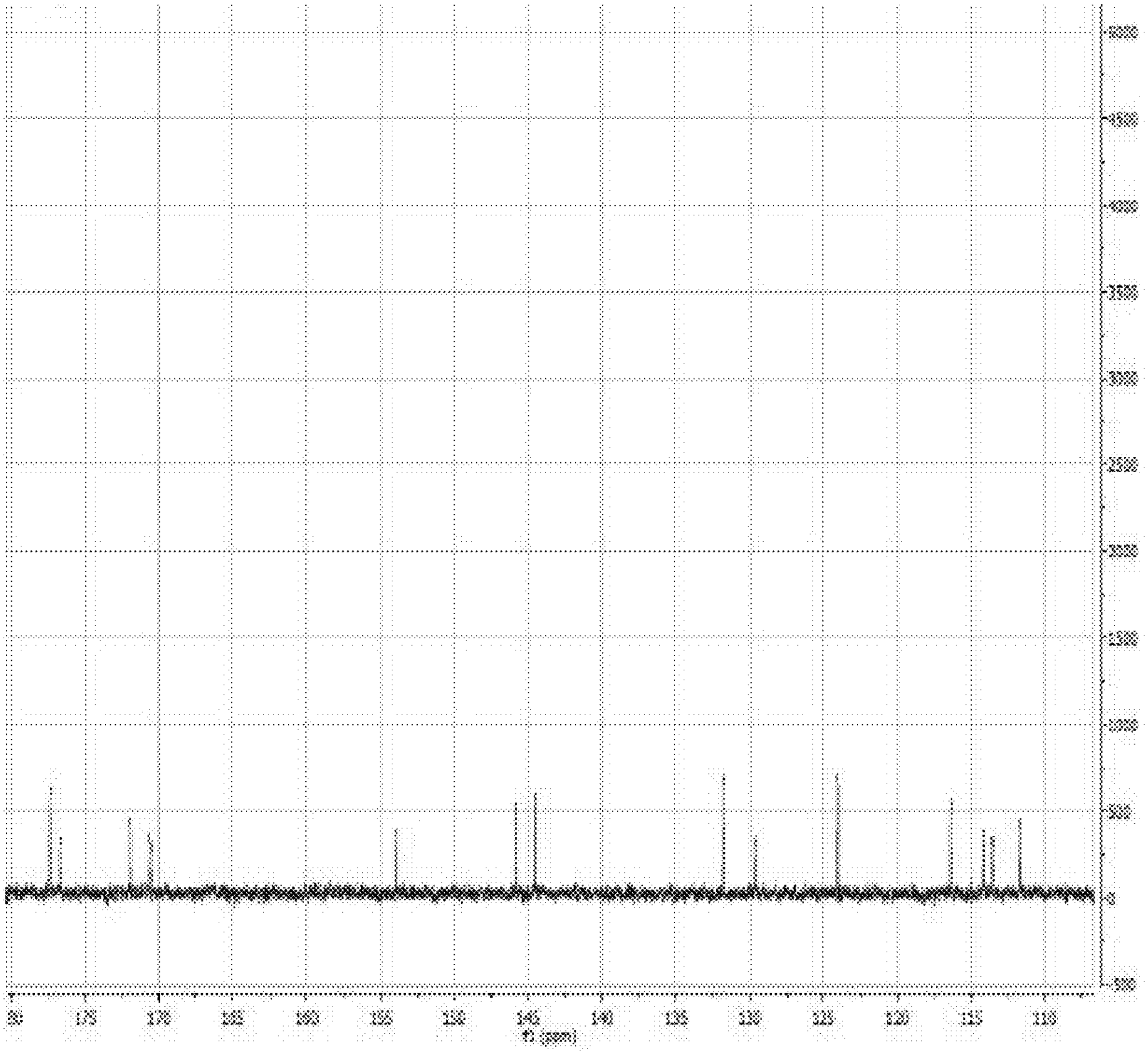
Figure 19:
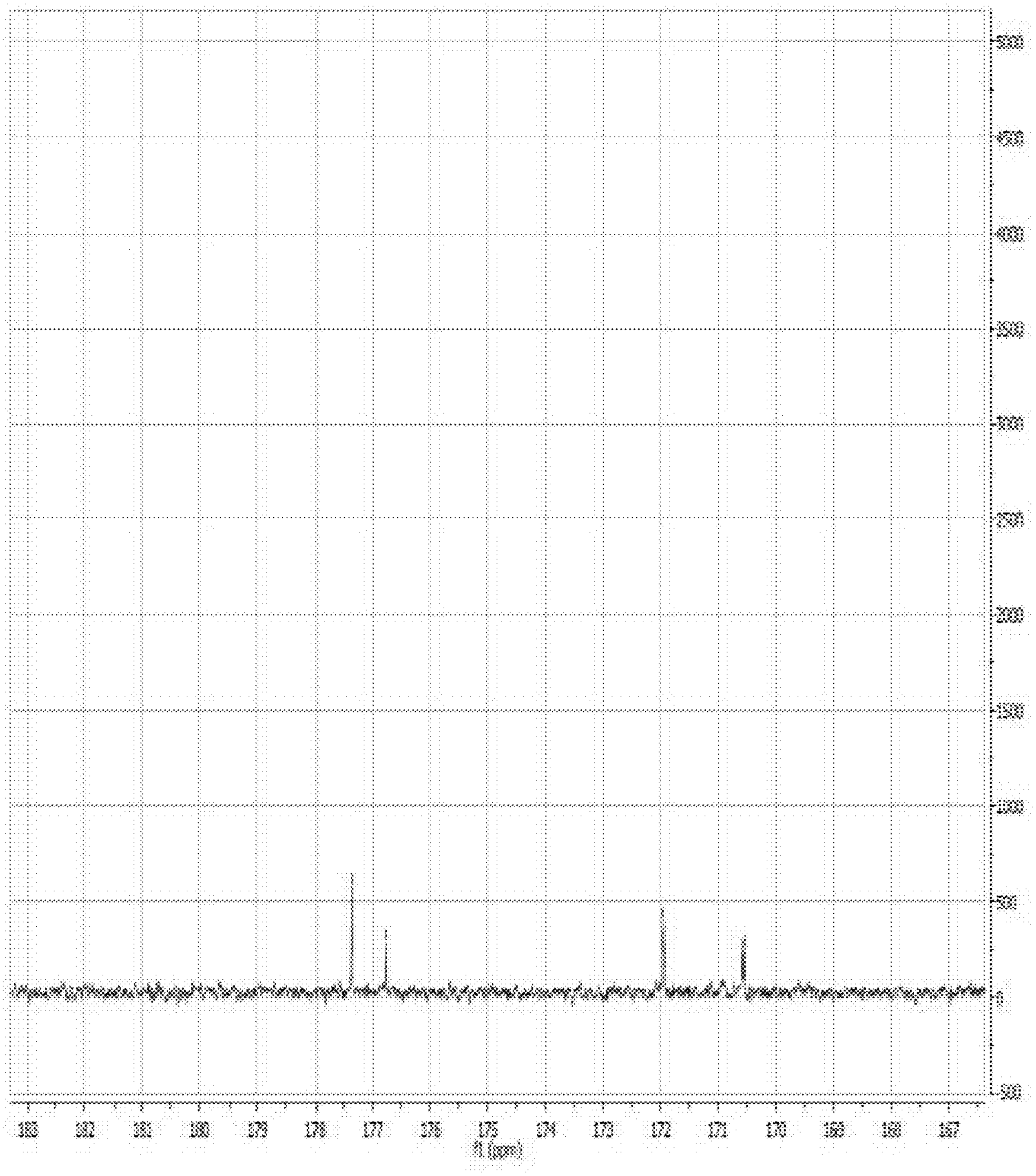
Figure 20:
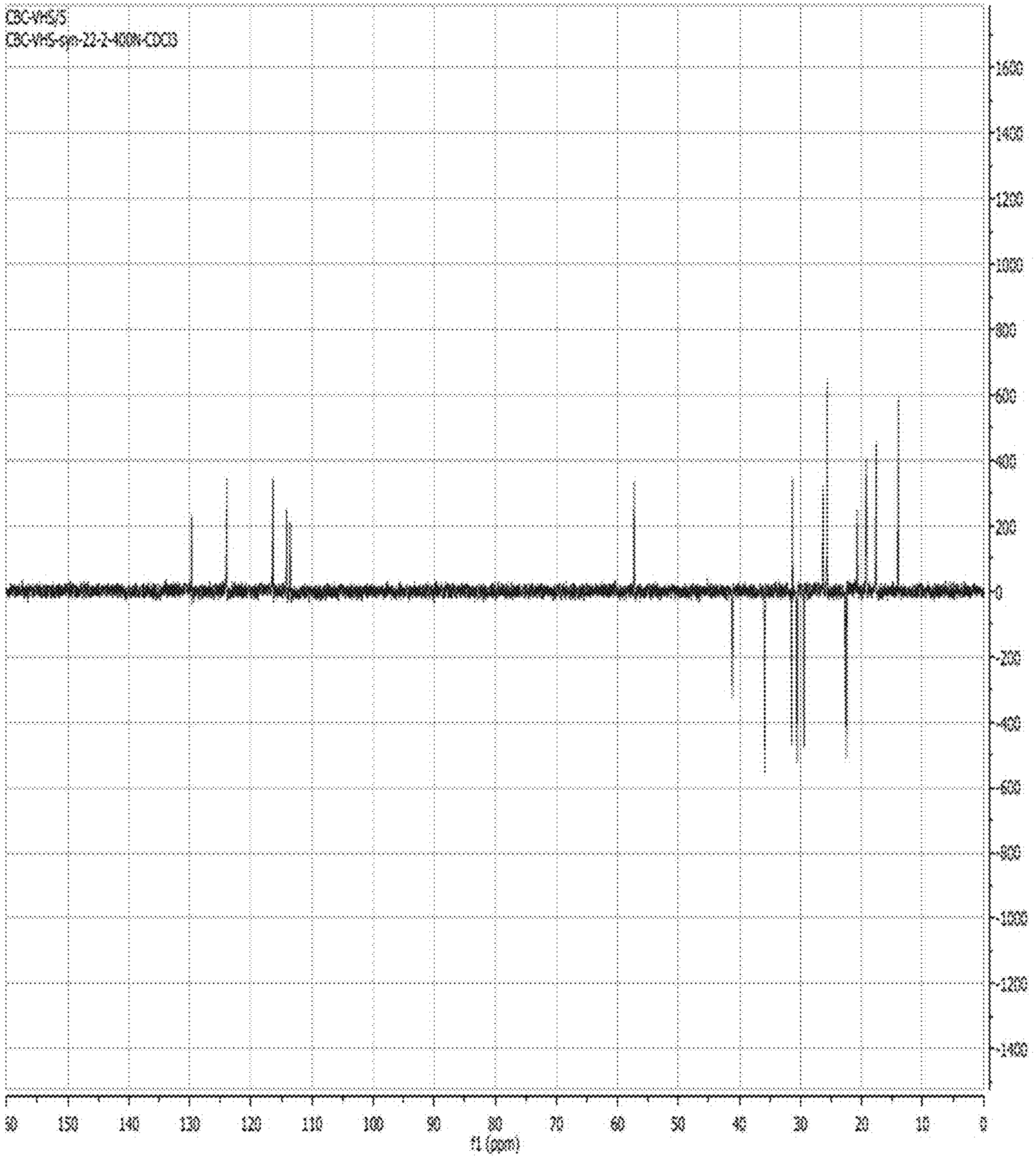
Figure 21:
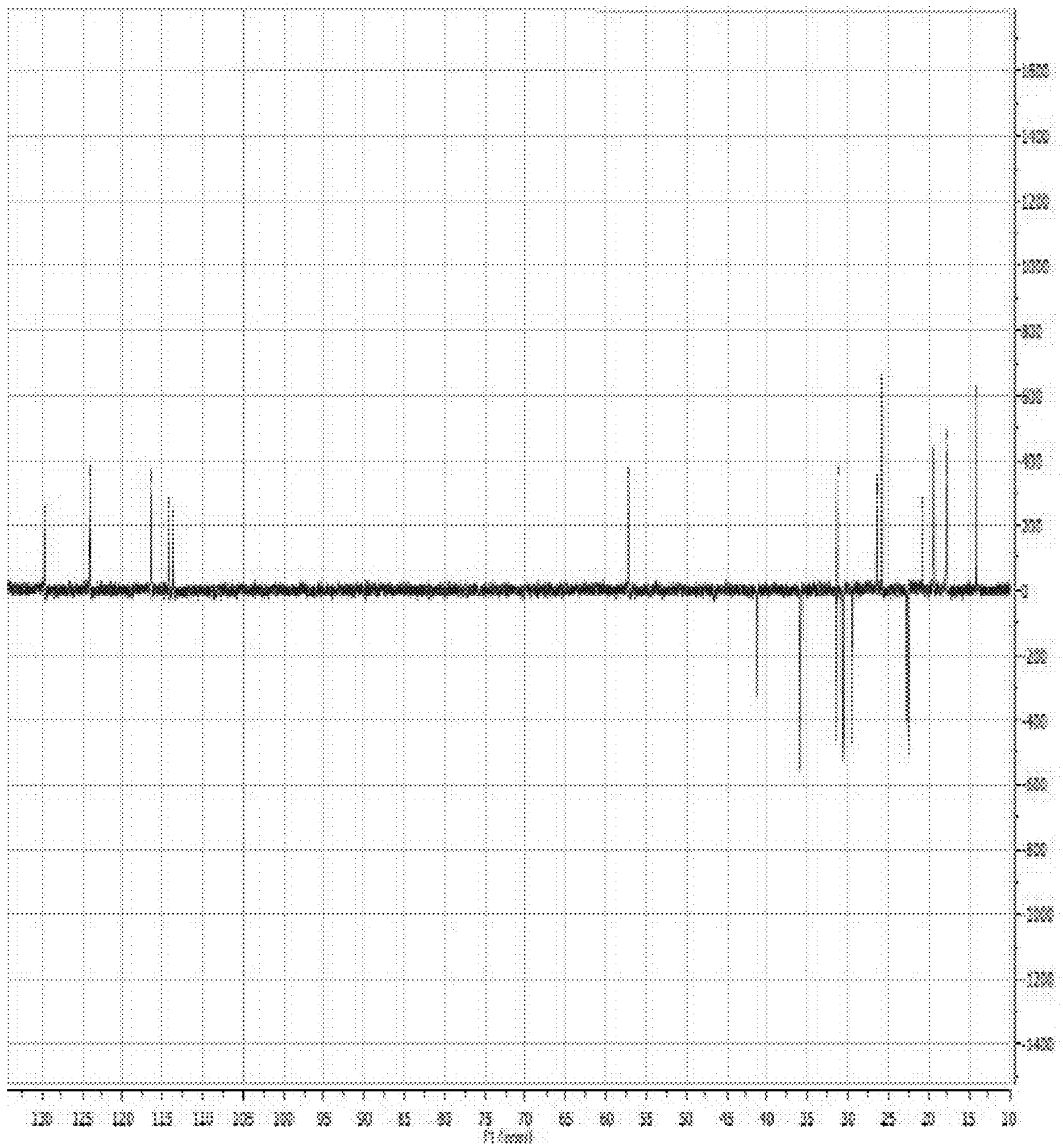
Figure 22:
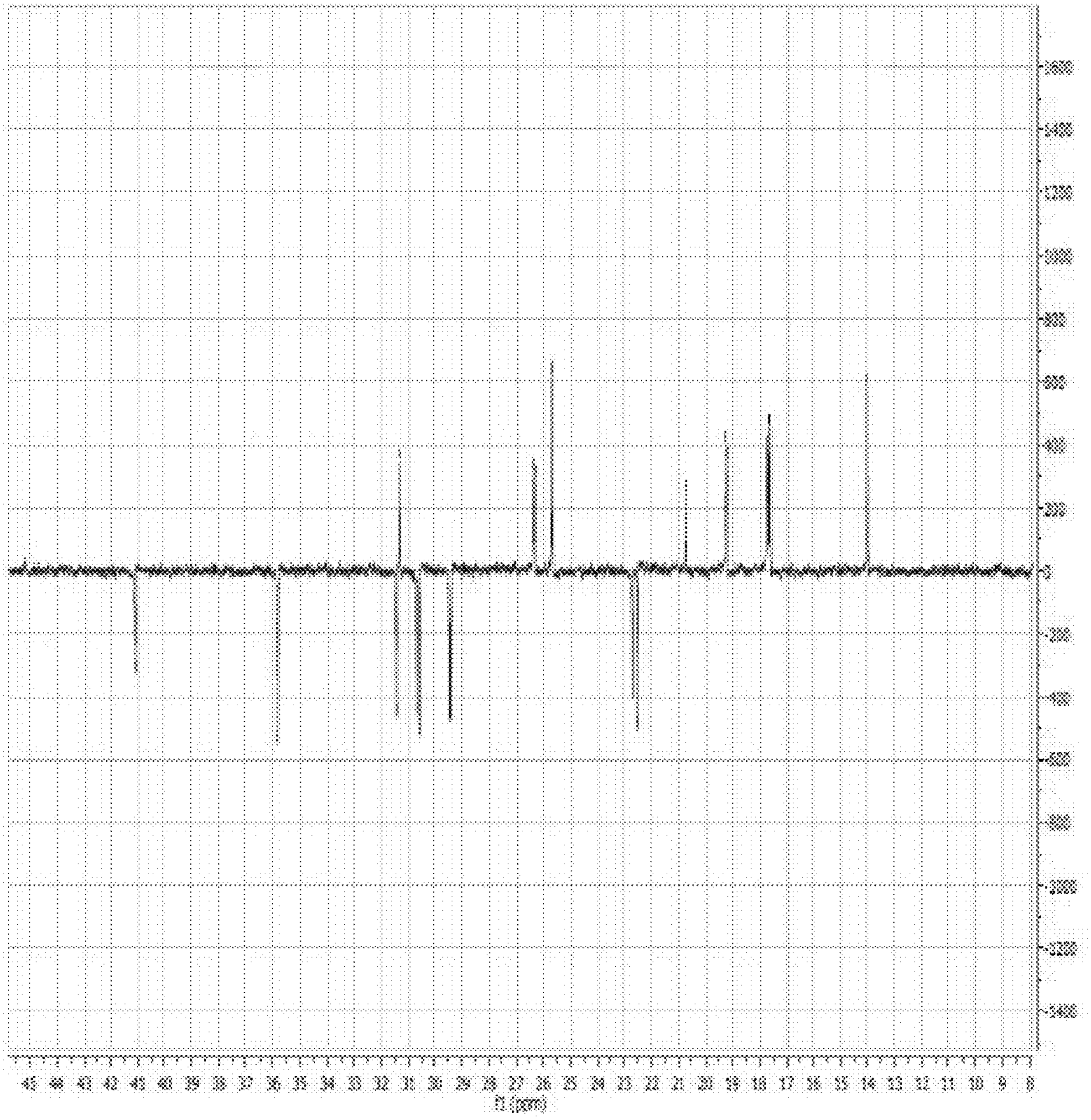
Figure 23:
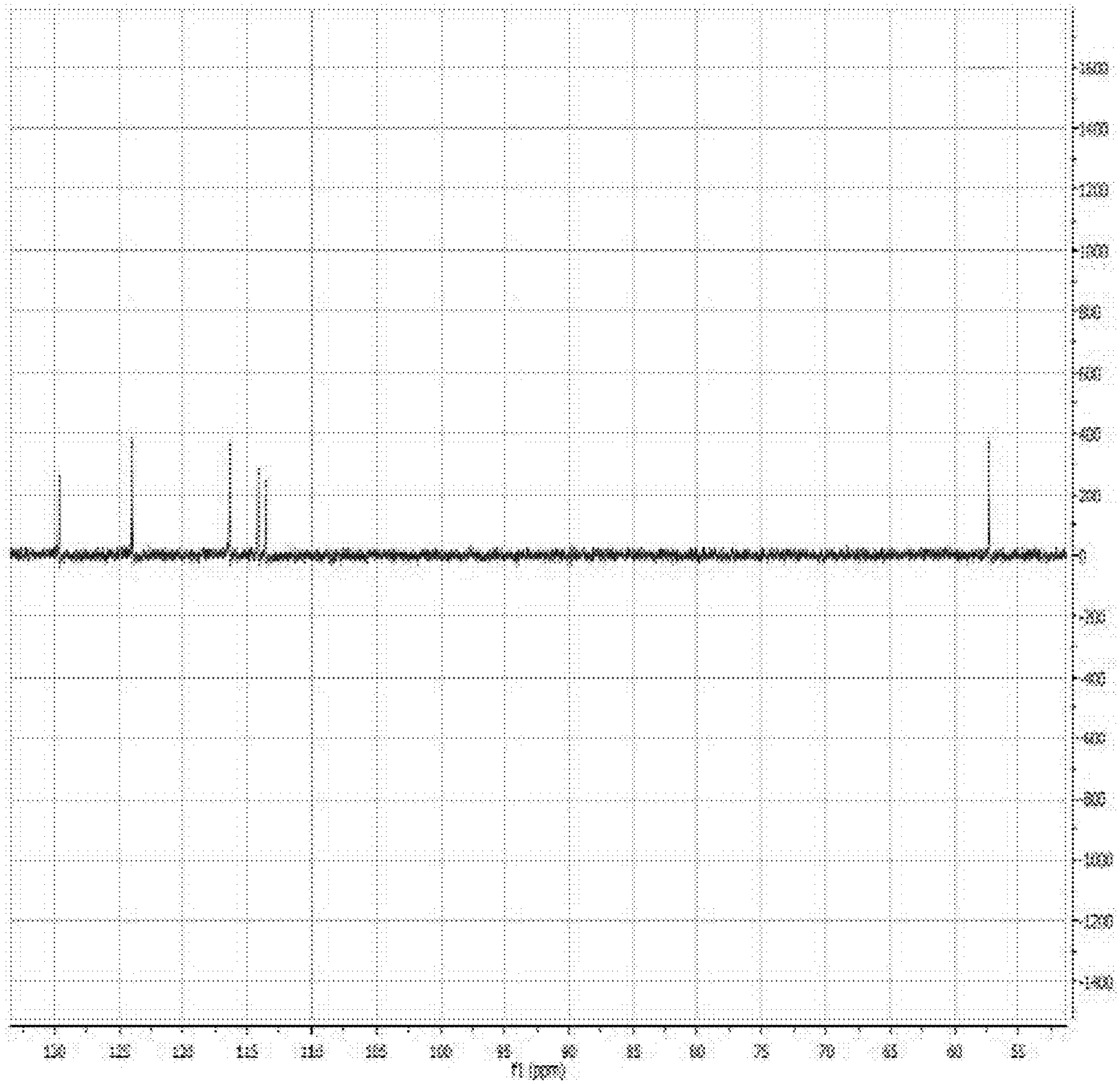
Figure 24:
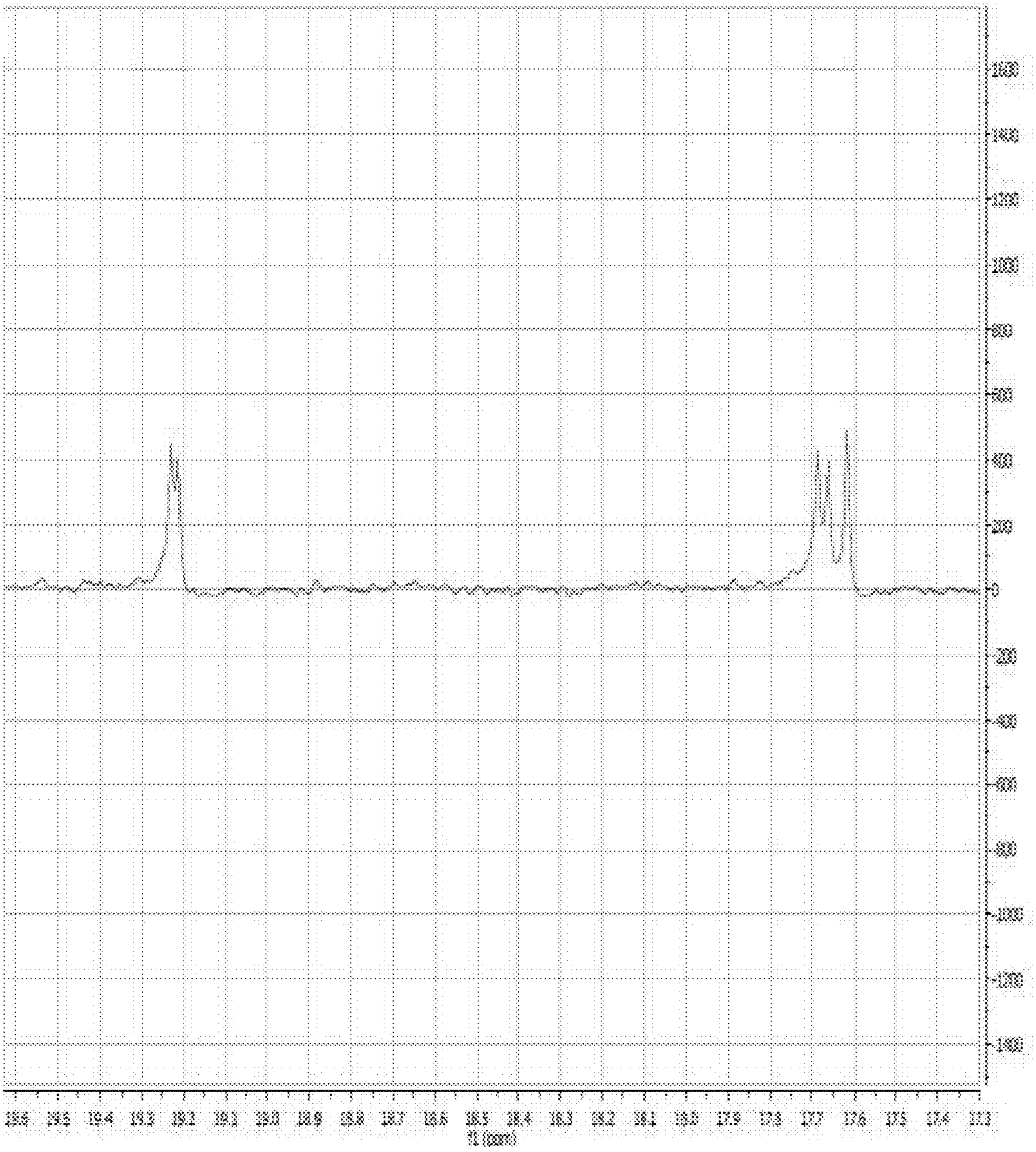
Figure 25:
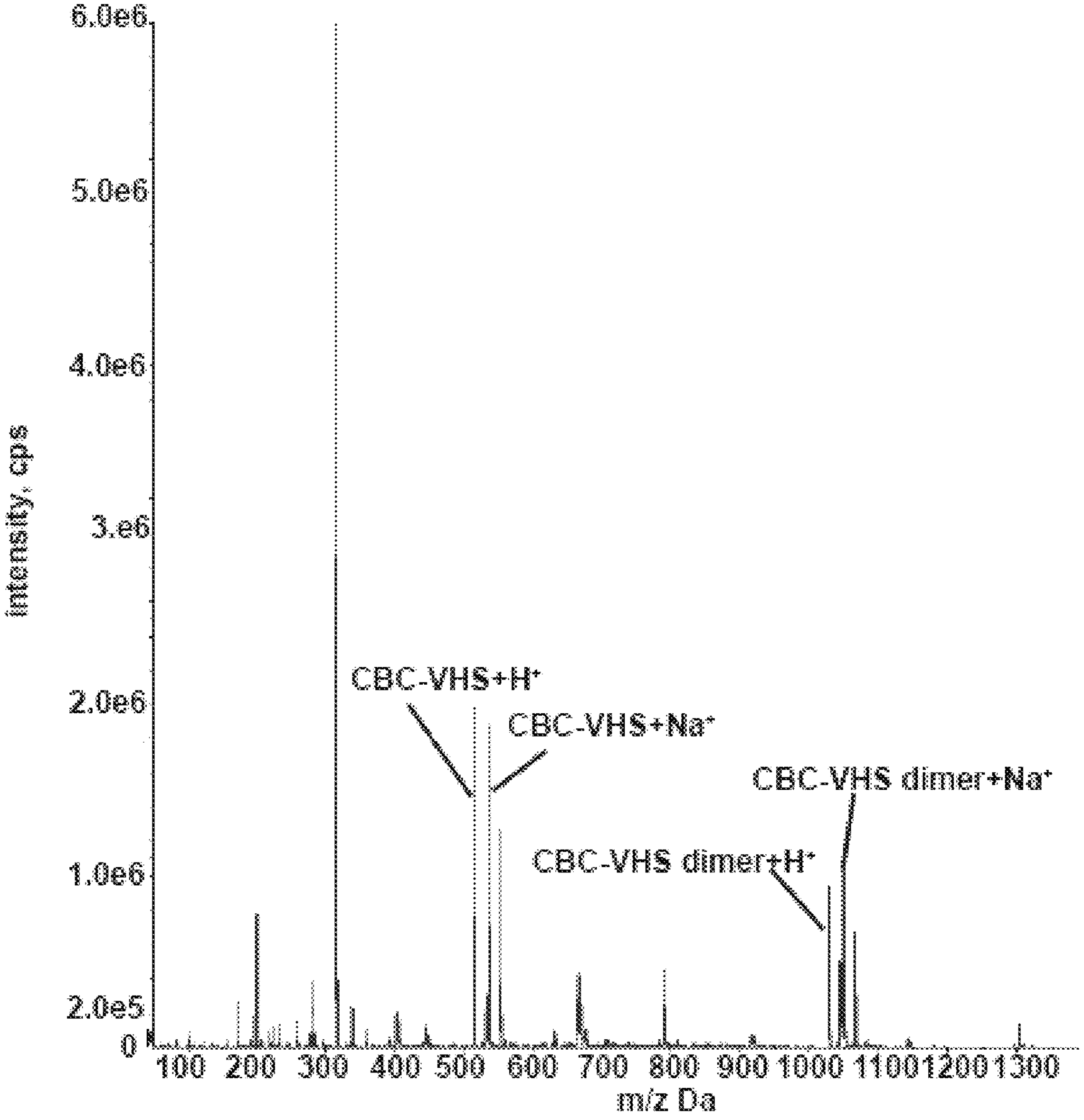
Figure 26:
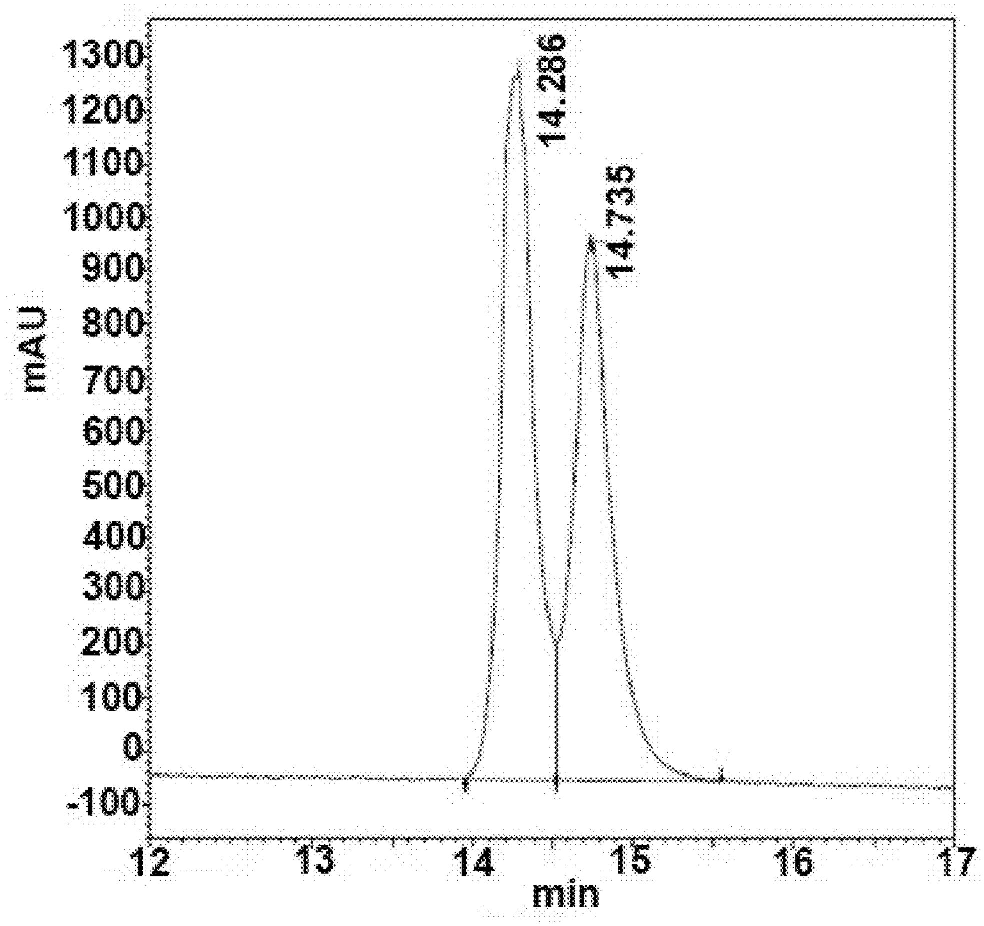
Figure 27:
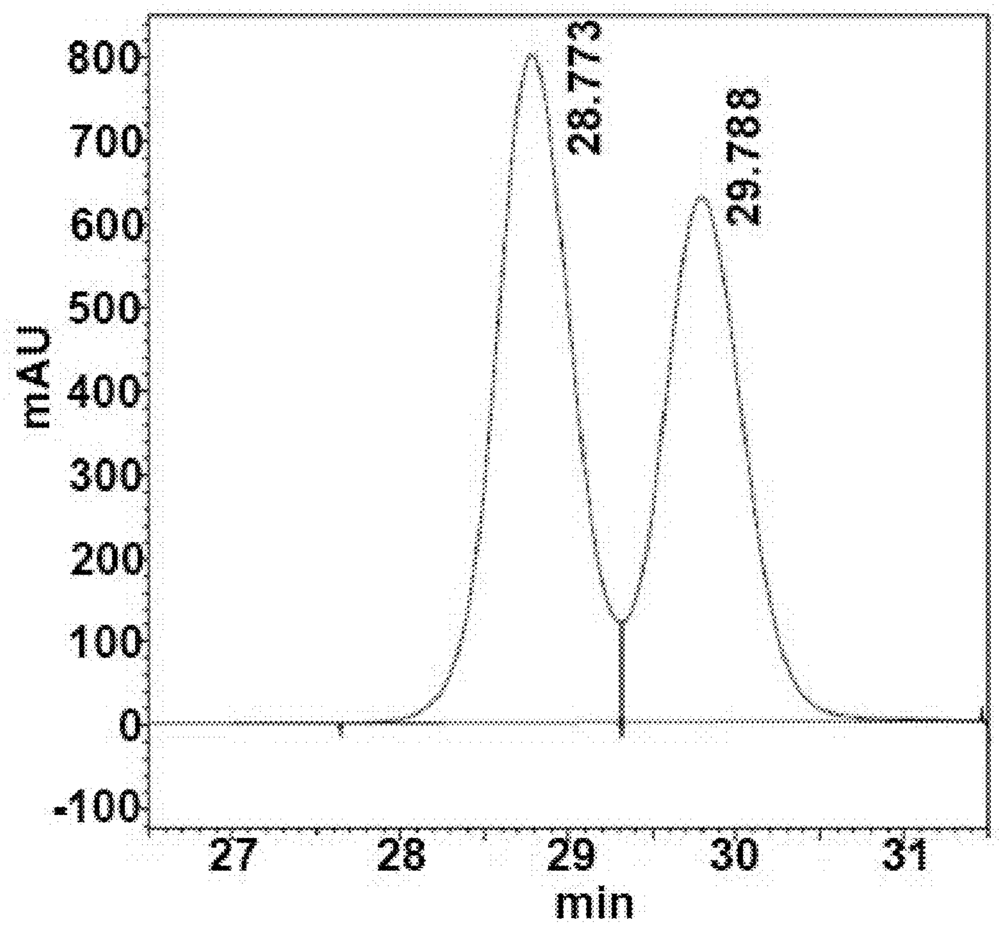
Figure 28:
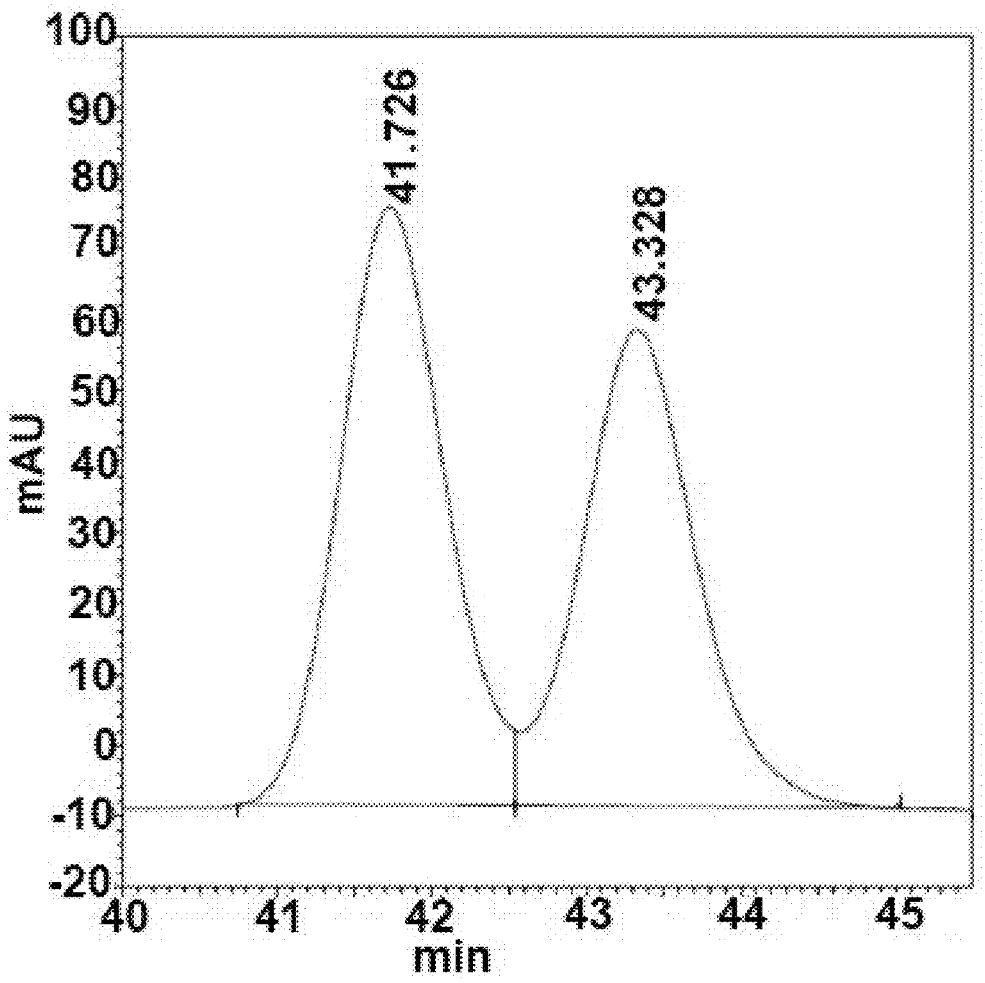
Figure 29A:
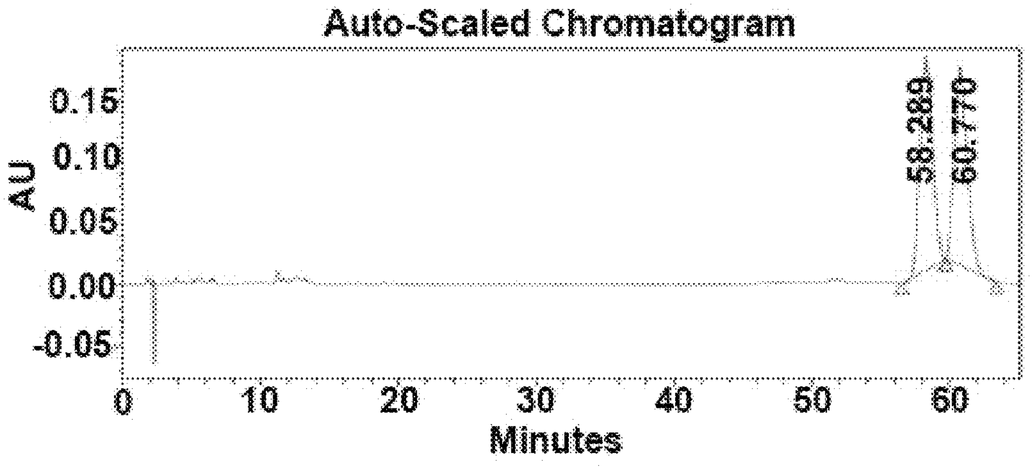
Figure 29B:
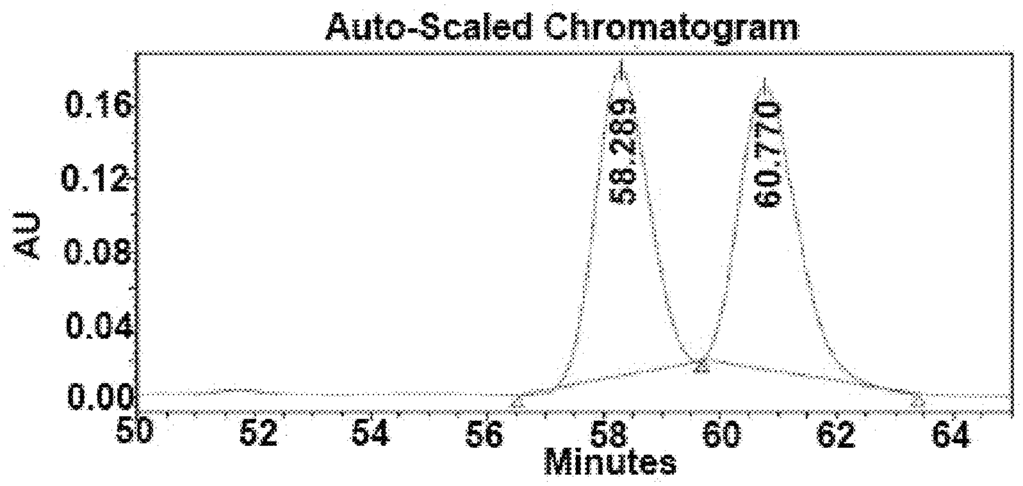

As CBC-Val-HS is racemic in nature, two diastereoisomers of CBC-Val-HS were isolated and assessed for efficacy in the mouse model of abdominal writhing. Once again, CBC-Val-HS was as effective as CBC within this task (One-way ANOVA post-hoc Bonferroni multiple comparison, $F=8.60$, $p<0.001$ each). Both diastereoisomers of CBC-Val-HS (isomer 1 and isomer 2) were also effective ($p<0.001$ and $p=0.037$), with no statistical differences detected between the two isomers or the racemic CBC-Val-HS ($p=0.81$). Similarly, racemic CBC-Val-HS, and each diastereoisomer of CBC-Val-HS displayed anti-nociceptive potential against thermal pain in the hotplate test (One-way ANOVA post-hoc Bonferroni multiple comparison, $F=8.79$, $p=0.02$ and 0.045), with no differences detected between groups. Results are provided in FIGS. 4A-4B.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claim.

REFERENCES

1. Li. I, Zhang, Y. Emerging drug targets for pain treatment. Eur J Pain, 2012; 681:1-5.
2. Nahin R L, Sayer 8, Stussman B J, et al. Eighteen-Year Trends in the Prevalence of, and Health Care Use for, Noncancer Pain in the United States: Data from the Medical Expenditure Panel. J Pain, 2019; 20:796-809.
3. Kalso E, Edwards J E, Moore A R, et al. Opioids in chronic non-cancer pain: Systematic review of efficacy and safety. Pain, 2004; 112:372-380.
4. Wilson N, Kariisa M, Seth P, et al. Drug and Opioid-Involved Overdose Deaths—MMWR Morb Mortal Wkly Rep, 2020; 69:290-297.
5. Hutchison K E, Hagerty S L, Galinkin J, et al. Cannabinoids, Pain, and Opioid Use Reduction: The Importance of Distilling and Disseminating Existing Data. Cannabis Cannabinoid Res. 2019 4:3, 158-164.
6. Chiou L C, Hu S S, Ho Y C. Targeting the cannabinoid system for pain relief? Acta Anaesthesiol Taiwan, 2013; 51:161-70.
7. Hill K P, Palastro M D, Johnson 8, et al. Cannabis and Pain: A Clinical Review. Cannabis Cannabinoid Res. 2017 2: I, 96-104
8. Kehl L J, Hamamoto D T, Wacnik P W, et al. A cannabinoid agonist differentially attenuates deep tissue hyperalgesia in animal models of cancer and inflammatory muscle pain. Pain, 2003; I 03:175-186.
9. Lotsch J, Weyer-Menkhoff I, Tegeder I. Current evidence of cannabinoid-based analgesia obtained in preclinical and human experimental settings. Eur J Pain, 2017; 22:471-484.
10. Harris H M, Rousseau M A, Wanas A S, et al. Role of Cannabinoids and Terpenes in Cannabis-Mediated Analgesia in Rats. Cannabis Cannabinoid Res. 2019; 4 (3): 177-182.
11. Agarwal N, Pacher P, Tegeder I, et al. Cannabinoids mediate analgesia largely via peripheral type I cannabinoid receptors in nociceptors. Nat Neurosci. 2007 July; I0 (7): 870-9.
12. MacCallum C A, Russo E B. Practical considerations in medical cannabis administration and dosing. Eur. J. Intern. Med, 2018; 49:12-19.
13. ElSohly M A, Slade D. Chemical constituents of marijuana: The complex mixture of natural cannabinoids. Life Sciences, 2005; 78:539-548.
14. Turner C E & ElSohly M A. Biological activity of cannabichromene, its homologs and isomers. J Clin Phannacol, 1981; 21 SI, 283S-29 IS.
15. Wirth P W, Watson E S, Elsohly M A, et al. Anti-inflammatory properties of cannabichromene. Life Sci, 1980; 26:1991-1995.
16. DeLong G T, Wolf C E, Polis A, et al. Pharmacological Evaluation of the Natural Constituent of Cannabis Sativa, Cannabichromene and its Modulation by t-.9-Tetrahydro-cannabinol. Drug Alcohol Depend, 2011; 112:126-133.
17. Izzo A A, Capasso R, Aviello G, et al. Inhibitory effect of cannabichromene, a major non-psychotropic cannabinoid extracted from Cannabis saliva, on inflammation-induced hypermotility in mice. Br J Pharmacol, 2012; 166:1444-1460.
18. Davis W, Hatoum N S. Neurobehavioral actions of cannabichromene and interactions with delta-.9-tetrahydrocannabinol. Gen Pharmacol, 1983; 14:24 7-252.
19. Booker L, Naidu P S, Razdan R K, et al. Evaluation of prevalent phytocannabinoids in the acetic acid model of visceral nociception. Drug Alcohol Depend, 2009; 105 (1-2): 42-4 7.

The invention claimed is:

1. A compound having the structure I or a pharmaceutically acceptable salt thereof

I

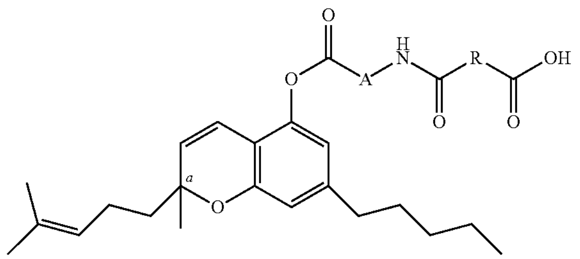

wherein

A is a residue of an amino acid or an alkyl group;

R is an alkyl group or an aryl group; and the stereochemistry at carbon a is substantially R, substantially S, or racemic.

2. The compound of claim 1, wherein A is a residue of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

3. The compound of claim 1, wherein A is a residue of valine.

4. The compound of claim 1, wherein A is an alkyl group having 1 to 10 carbon atoms.

5. The compound of claim 1, wherein R is a $C_1$ to $C_{10}$ alkyl group.

6. The compound of claim 1, wherein R is $(CH_2)_n$, where n is an integer from 1 to 3.

7. The compound of claim 1, wherein the stereochemistry at carbon a is racemic.

8. The compound of claim 1, wherein the compound has the structure II

II

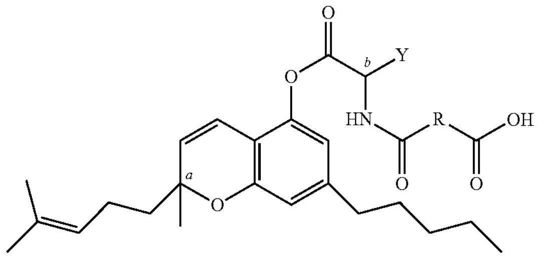

wherein Y is an alkyl group, and the stereochemistry at carbon b is substantially R, substantially S, or racemic.

9. The compound of claim 8, wherein R is a $C_1$ to $C_{10}$ alkyl group and Y is $C_1$ to $C_{10}$ alkyl group.

10. The compound of claim 8, wherein the stereochemistry at carbon a is substantially R or substantially S, and the stereochemistry at carbon b is substantially R or substantially S.

11. The compound of claim 8, wherein the stereochemistry at carbon a is racemic.

12. The compound of claim 1, wherein the compound has the structure III

III

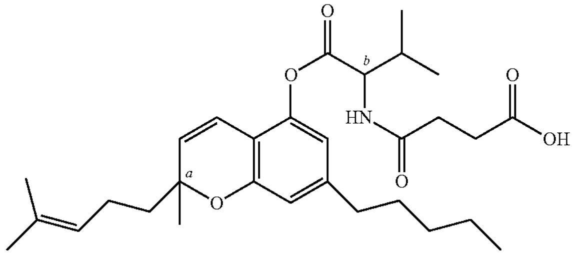

wherein the stereochemistry at carbon a is substantially R, substantially S, or racemic, and the stereochemistry at carbon b is substantially R or substantially S.

13. The compound of claim 12, wherein the stereochemistry at carbon a is racemic.

14. The compound of claim 1, wherein the compound is produced by the process comprising:

(a) reacting cannabichromene with a protected amino acid to produce a protected amino ester;

(b) deprotecting the protected amino ester to produce the deprotected amino ester; and (c) reacting the deprotected amino ester with an anhydride.

15. The compound of claim 14, wherein after step (c), when two diastereoisomers are produced, separating the two diastereoisomers from each other.

16. A pharmaceutical composition comprising the compound of claim 1 and a pharmaceutically acceptable carrier.

17. A method for treating or preventing pain in a subject in need thereof comprising administering to the subject the compound of claim 1.

18. The method of claim 17, wherein the patient is experiencing acute or chronic pain.

19. The method of claim 17, wherein the patient is experiencing pain caused by a chemotherapeutic agent or as a result of a surgical procedure.

20. The method of claim 17, wherein the compound or composition is administered orally or parenterally.

* * * * *